US012686676B2

(12) United States Patent
Tanaka et al.

(10) Patent No.: US 12,686,676 B2
(45) Date of Patent: Jul. 21, 2026

(54) COMPOUND, ENDOTHELIN-A RECEPTOR ANTAGONIST, AND PHARMACEUTICAL COMPOSITION

(71) Applicant: Alchemedicine, Inc., Tsukuba (JP)

(72) Inventors: Keigo Tanaka, Tsukuba (JP); Tomohisa Ninomiya, Tsukuba (JP); Yoshihide Tomata, Tsukuba (JP)

(73) Assignee: ALCHEMEDICINE, INC., Ibaraki (JP)

(*) Notice: Subject to any disclaimer, the term of this patent is extended or adjusted under 35 U.S.C. 154(b) by 283 days.

(21) Appl. No.: 18/566,804

(22) PCT Filed: Jun. 21, 2022

(86) PCT No.: PCT/JP2022/024638
§ 371 (c)(1),
(2) Date: Dec. 4, 2023

(87) PCT Pub. No.: WO2022/270487
PCT Pub. Date: Dec. 29, 2022

(65) Prior Publication Data
US 2024/0287053 A1 Aug. 29, 2024

(30) Foreign Application Priority Data
Jun. 22, 2021 (JP) ................................. 2021-103047

(51) Int. Cl.

| | |
|---|---|
| ***C07D 413/14*** | (2006.01) |
| ***A61K 31/4439*** | (2006.01) |
| ***A61K 31/497*** | (2006.01) |
| ***A61P 9/12*** | (2006.01) |
| ***C07D 405/14*** | (2006.01) |

(52) U.S. Cl.
CPC ........ *C07D 413/14* (2013.01); *A61K 31/4439* (2013.01); *A61K 31/497* (2013.01); *A61P 9/12* (2018.01); *C07D 405/14* (2013.01)

(58) Field of Classification Search
CPC C07D 413/14; C07D 405/14; A61K 31/4439; A61K 31/497; A61P 9/12; A61P 9/08; A61P 11/00; A61P 13/12; A61P 25/02; A61P 35/00; A61P 43/00; A61P 1/16; A61P 9/04
See application file for complete search history.

(56) References Cited

U.S. PATENT DOCUMENTS

| | | |
|---|---|---|
| 5,514,696 A | 5/1996 | Murugesan et al. |
| 5,612,359 A | 3/1997 | Murugesan |
| 2013/0197045 A1 | 8/2013 | Tanaka et al. |

FOREIGN PATENT DOCUMENTS

| | | | |
|---|---|---|---|
| WO | WO-1994027979 A1 | 12/1994 | |
| WO | WO 1996/031492 A1 | 10/1996 | |
| WO | WO 1996/040681 A1 | 12/1996 | |
| WO | WO 1998/013366 A1 | 4/1998 | |
| WO | WO 1998/033780 A1 | 8/1998 | |
| WO | WO 1998/033781 A1 | 8/1998 | |
| WO | WO 1998/049162 A1 | 11/1998 | |
| WO | WO 2001/049685 A2 | 7/2001 | |
| WO | WO 2004/035057 A1 | 4/2004 | |
| WO | WO 2013/115162 * | 8/2013 | .......... C07D 413/14 |
| WO | WO 2013/115162 A1 | 8/2013 | |

OTHER PUBLICATIONS

Rubin L, et al., "Bosentan Therapy for Pulmonary Arterial Hypertension." N Engl J Med, vol. 346, No. 12 (Mar. 21, 2022).
Maki H, et al., "The Clinical Efficacy of Endothelin Receptor Antagonists in Patients with Pulmonary Arterial Hypertension." Int Heart J 2020; 61: 799-805 (Jul. 30, 2020).
Trachtman H, et al., "DUET: A Phase 2 Study Evaluating the Efficacy and Safety of Sparsentan in Patients with FSGS." J Am Soc Nephrol 29: 2745-2754, (Nov. 2018). ISSN: 1046-6673/2911-2745.
Nakamura T, et al., "Effect of a Specific Endothelin Receptor A Antagonist on Glomerulonephritis of ddY Mice with IgA Nephropathy." Nephron 1996:72:454-460. Published online Dec. 18, 2008. Downloaded by: r. yoshida—650450 122.208.38.42—Apr. 20, 2022 10:47:59 AM.
Heerspink H, et al., Atrasentan and renal events in patients with type 2 diabetes and chronic kidney disease (SONAR): a double-blind, randomised, placebo-controlled trial. Lancet 2019; 393: 1937-47, www.thelancet.com vol. 393 May 11, 2019.
(Continued)

*Primary Examiner* — Rebecca L Anderson
*Assistant Examiner* — David M Shim
(74) *Attorney, Agent, or Firm* — Sterne, Kessler, Goldstein & Fox P.L.L.C.

(57) ABSTRACT

An object of the present invention is to provide a compound having an ETA receptor antagonistic effect, etc. The object can be attained by a compound represented by the following formula (1):

(1)

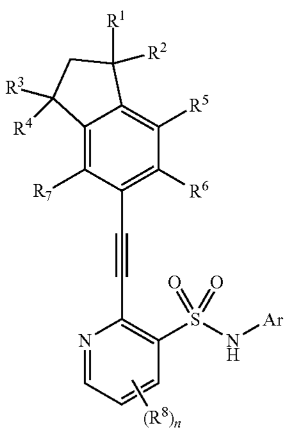

wherein variables are as described herein, or a pharmaceutically acceptable salt thereof.

20 Claims, No Drawings

(56) References Cited

OTHER PUBLICATIONS

Dhaun N, et al., "Selective Endothelin-A Receptor Antagonism Reduces Proteinuria, Blood Pressure, and Arterial Stiffness in Chronic Proteinuric Kidney Disease." Hypertension 57:772-779 (2011) (epub Feb. 28, 2011) Downloaded from http://hyper.ahajournals.org. by guest on May 10, 2017. DOI: 10.1161/HYPERTENSIONAHA.110.167486.
Kasztan M, et al., "Long-Term Endothelin-A Receptor Antagonism Provides Robust Renal Protection in Humanized Sickle Cell Disease Mice." J Am Soc Nephrol 28: 2443-2458, (Aug. 2017). doi: https://doi.org/10.1681/ASN.2016070711. ISSN : 1046-6673/2808-2443.
Wilhelm S.M. et al., "The Use of The Endothelin Receptor Antagonist, Tezosentan, Before or After Renal Ischemia Protects Renal Function." vol. 71, 211-216, No. 2, Jan. 27, 2001 0041-1337/01/7102-211/0 Transplantation. Lippincott Williams & Wilkins, Inc.
Dhaun, N, et al., "Role of Endothelin-1 in Clinical Hypertension." (Hypertension. 2008;52:452-459 (September) epub Aug. 4, 2008. Hypertension is available at http://hyper.ahajournals.org. DOI: 10.1161/HYPERTENSIONAHA.108.117366. American Heart Association, Inc.
Demirci E, et al., "Endothelin Receptor Inhibition with Bosentan Delays Onset of Liver Injury in Streptozotocin-Induced Diabetic Condition." Drug Res (Stugg) May 2015 65(5):272-280.
Okamoto T, et al., "Antifibrotic effects of ambrisentan, an endothelin-A receptor antagonist, in a non-alcoholic steatohepatitis mouse model." World J Hepatol Aug. 8, 2016; 8(22): 933-941. ISSN 1948-5182 (online). Baishideng Publishing Group Inc. DOI: 10.4254/wjh.v8.122.933.
Degertekin B, et al., "The Serum Endothehn-1 Level in Steatosis and NASH, and Its Relation with Severity of Liver Fibrosis." Dig Dis Sci (Apr. 2007) 52:2622-2628 DOI 10.1007/s10620-006-9147-8. Springer Science+Business Media. Inc.
Rosanò L, et al., "Endothelin 1 in cancer: biological implications and therapeutic opportunities." Nature Reviews Cancer vol. 13, Sep. 2013, 637-651. Macmillan Publishers Limited.
Yoshino O, et al., "Bradykinin system is involved in endometriosis-related pain through endothelin-1 production." E J Pain 22 (Mar. 2018) 501-510. European Pain Federation.
Abaé M, et al., "Immunoreactive endothelin-1 concentrations in follicular fluid of women with and without endometriosis undergoing in vitro fertilization-embryo transfer." Fertility and Sterility vol. 61(6):1083-1087, Jun. 1994; presented in part at the $48^{th}$ Ann. Meeting of the American Fertility Society, New Orleans, Louisiana, Oct. 31 to Nov. 5, 1992.
Shetty N, et al., "Endothelin Receptor Antagonists as Disease Modifiers in Systemic Sclerosis." Inflammation & Allergy—Drug Targets 10: 19-26 (Feb. 2011).
Matucci-Cerinic M, et al., "Bosentan treatment of digital ulcers related to systemic sclerosis: results from the RAPIDS-2 randomised, double-blind, placebo-controlled trial." Ann Rheum Dis 2011;70:32-38 (Jan). doi: 10.1136/ard.2010.130658. Ann Rheum Dis: first published as 10.1136/ard.2010.130658 on Aug. 30, 2010. Downloaded from http://ard.bmj.com/ on Mar. 17, 2021 by guest.
Cheng Y.W., et al., "Role of endothelin-1 and its receptors in cerebral vasospasm following subarachnoid hemorrhage." Molecular Medicine Reports 18: 5229-5236, Dec. 2018. DOI: 10.3892/mmr.2018.9513.
Tanaka A, et al., Endothelin-1 Induces Myofibrillar Disarray and Contractile Vector Variability in Hypertrophic Cardiomyopathy-Induced Pluripotent Stem Cell-Derived Cardiomyocytes. DOI: 10.1161/JAHA.114.001263. Journal of the American Heart Assoc. 2014;3:e001263 (Nov. 11). Downloaded from http://jaha.ahajournals.org/ at Eisai Co Ltd—Tsukuba-Shi on Feb. 18, 2016.
Opitz C, et al., "Inhibition of endothelin receptors in the treatment of pulmonary arterial hypertension: does selectivity matter?" European Heart Journal (Aug. 2008) 29, 1936-1948 doi:10.1093/eurheartj/ehn234.
Davenport A, et al., "Endothelin." http://dx.doi.org/10.1124/pr.115.011833, Pharmacol Rev 68:357-418, Apr. 2016. Downloaded from pharmrev.aspetjournals.org at ASPET Journals on Aug. 14, 2023.
Schneider M, et al., "Contrasting Actions of Endothelin $ET_A$ and $ET_B$ Receptors in Cardiovascular Disease." Annu Rev Pharmacol Toxicol. (Feb. 2007); 47: 731-759. doi:10.1146/annurev.pharmtox.47.120505.105134.
International Search Report for PCT/JP2022/024638; I.A. fd Jun. 21, 2022, mailed Jul. 26, 2022, by the Japan Patent Office, Tokyo, Japan.
International Report on Patentability for PCT/JP2022/024638; I.A. fd Jun. 21, 2022, issued Dec. 14, 2023, by the International Bureau of WIPO, Geneva, Switzerland.

* cited by examiner

COMPOUND, ENDOTHELIN-A RECEPTOR ANTAGONIST, AND PHARMACEUTICAL COMPOSITION

BACKGROUND OF THE INVENTION

Field of the Invention

The present invention relates to a compound, an endothelin A receptor antagonist and a pharmaceutical composition.

Description of the Related Art

Endothelin (ET) is a peptide derived from vascular endothelial cells, and has a vasoconstrictive effect. An endothelin A (ETA) receptor and an endothelin B (ETB) receptor are known as receptors of endothelin. The ETA receptor is involved in vasoconstriction, central sympathetic activation, aldosterone secretion promotion, and the like. The ETB receptor is involved in vasodilatation, endothelin clearance, and the like.

The ETA receptor is reportedly related to various diseases. For example, there are reports on the relation of the ETA receptor to pulmonary hypertension (e.g., The New England Journal of Medicine, 2002, 346, pp 896-903; and International Heart Journal, 2020, 61, pp 799-805), focal segmental glomerulosclerosis (e.g., Journal of the American society of Nephrology, 2018, 29, pp 2745-2754), IgA nephropathy (e.g., Nephron, 1996, 72, pp 454-460), chronic kidney disease (including diabetic nephropathy) (e.g., The Lancet, 2019, 393, pp 1937-1947; and Hypertension, 2011, 57, pp 772-779), renal damage associated with sickle cell syndrome (e.g., Journal of the American society of Nephrology, 2017, 28, pp 2443-2458), acute kidney injury (e.g., Transplantation, 2001, 71, pp 211-216), hypertension (e.g., Hypertension, 2008, 52, pp 452-459), non-alcoholic steatohepatitis (NASH) (e.g., Drug Research, 2015, 65, pp 272-280; World Journal of Hepatology, 2016, 8, pp 933-941; and Digestive Diseases and Sciences, 2007, 52, pp 2622-2628), cancer (e.g., Nature reviews cancer, 2013, 13, pp 637-651), pain associated with endometriosis (e.g., European Journal of Pain, 2018, 22, pp 501-510; and Fertility and Sterility, 1994, 61, pp 1083-1087), complications associated with scleroderma (e.g., Inflammation & Allergy—Drug Targets, 2011, 10, pp 19-26; and Annals of the Rheumatic Diseases, 2011, 70, pp 32-38), cerebral vasospasm (e.g., Molecular medicine reports, 2018, 18, pp 5229-5236), and hypertrophic cardiomyopathy (e.g., Journal of the American Heart Association, 2014, 3, e00126).

Various compounds having an ETA receptor antagonistic effect have been reported (e.g., U.S. Pat. Nos. 5,514,696 and 5,612,359, and International Publication Nos. WO 1996/40681, WO 1996/31492, WO 1998/49162, WO 1998/13366, WO 1998/33780, WO 1998/33781, WO 2001/49685, WO 2004/35057, and WO 2013/115162). In particular, sitaxentan having an ETA receptor antagonistic effect is known to selectively inhibit the ETA receptor in contrast to the ETB receptor, and has been reported to exhibit significant drug efficacy in clinical trials on pulmonary hypertension associated with connective tissue disease (European Heart Journal, 2008, 29, pp 1936-1948), to not increase endothelin concentrations in blood (Pharmacological Reviews, 2016, 68, pp. 357-418), and to not cause peripheral edema (Annual Review of Pharmacology and Toxicology, 2007, 47, pp 731-759).

Related Art Literatures

Patent Literature 1: U.S. Pat. No. 5,514,696
Patent Literature 2: U.S. Pat. No. 5,612,359
Patent Literature 3: WO 1996/40681
Patent Literature 4: WO 1996/31492
Patent Literature 5: WO 1998/49162
Patent Literature 6: WO 1998/13366
Patent Literature 7: WO 1998/33780
Patent Literature 8: WO 1998/33781
Patent Literature 9: WO 2001/49685
Patent Literature 10: WO 2004/35057
Patent Literature 11: WO 2013/115162
Non Patent Literature 1: The New England Journal of Medicine, 2002, 346, pp 896-903
Non Patent Literature 2: International Heart Journal, 2020, 61, pp 799-805
Non Patent Literature 3: Journal of the American society of Nephrology, 2018, 29, pp 2745-2754
Non Patent Literature 4: Nephron, 1996, 72, pp 454-460
Non Patent Literature 5: The Lancet, 2019, 393, pp 1937-1947
Non Patent Literature 6: Hypertension, 2011, 57, pp 772-779
Non Patent Literature 7: Journal of the American society of Nephrology, 2017, 28, pp 2443-2458
Non Patent Literature 8: Transplantation, 2001, 71, pp 211-216
Non Patent Literature 9: Hypertension, 2008, 52, pp 452-459
Non Patent Literature 10: Drug Research, 2015, 65, pp 272-280
Non Patent Literature 11: World Journal of Hepatology, 2016, 8, pp 933-941
Non Patent Literature 12: Digestive Diseases and Sciences, 2007, 52, pp 2622-2628
Non Patent Literature 13: Nature reviews cancer, 2013, 13, pp 637-651
Non Patent Literature 14: European Journal of Pain, 2018, 22, pp 501-510
Non Patent Literature 15: Fertility and Sterility, 1994, 61, pp 1083-1087
Non Patent Literature 16: Inflammation & Allergy—Drug Targets, 2011, 10, pp 19-26
Non Patent Literature 17: Annals of the Rheumatic Diseases, 2011, 70, pp 32-38
Non Patent Literature 18: Molecular medicine reports, 2018, 18, pp 5229-5236
Non Patent Literature 19: Journal of the American Heart Association, 2014, 3, e00126
Non Patent Literature 20: European Heart Journal, 2008, 29, pp 1936-1948
Non Patent Literature 21: Pharmacological Reviews, 2016, 68, pp. 357-418
Non Patent Literature 22: Annual Review of Pharmacology and Toxicology, 2007, 47, pp 731-759

An object of the present invention is to provide a compound having an ETA receptor antagonistic effect, and an ETA receptor antagonist or a pharmaceutical composition comprising the compound.

SUMMARY OF THE INVENTION

The present inventors have conducted diligent studies and consequently completed the present invention by finding that a compound having a specific structure has an ETA receptor antagonistic effect.

The present invention includes the following embodiments.

[1]

A compound represented by the following formula (1):

(1)

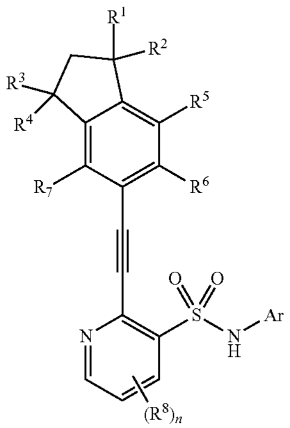

Wherein $R^1$ and $R^2$ are each independently hydrogen or alkyl, $R^3$ and $R^4$ are each independently hydrogen or alkyl, or $R^3$ and $R^4$ together form oxo, $R^5$ to $R^7$ are each independently hydrogen, alkyl, haloalkyl, halogen, alkoxy or haloalkoxy, each $R^8$ is independently alkyl, haloalkyl or halogen, n is an integer of 0 to 3, and Ar is represented by the following formula (Ar1) or (Ar2):

(Ar1)

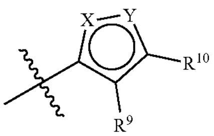

(Ar2)

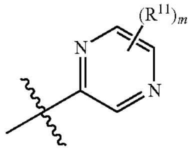

wherein

X and Y are nitrogen and oxygen, respectively, or oxygen and nitrogen, respectively, $R^9$ and $R^{10}$ are each independently hydrogen, alkyl, haloalkyl or halogen, each $R^{11}$ is independently alkyl, haloalkyl, halogen, alkoxy or haloalkoxy, and m is an integer of 0 to 3, or a pharmaceutically acceptable salt thereof.

[2]

The compound or the pharmaceutically acceptable salt thereof according to [1], wherein each of $R^1$ and $R^2$ is hydrogen.

[3]

The compound or the pharmaceutically acceptable salt thereof according to [1] or [2], wherein each of $R^5$ and $R^7$ is hydrogen, and $R^6$ is alkyl.

[4]

The compound or the pharmaceutically acceptable salt thereof according to any of [1] to [3], wherein n is 0.

[5]

The compound or the pharmaceutically acceptable salt thereof according to any of [1] to [4], wherein Ar is represented by formula (Ar1).

[6]

The compound or the pharmaceutically acceptable salt thereof according to any of [1] to [5], wherein each of $R^9$ and $R^{10}$ is alkyl.

[7]

The compound or the pharmaceutically acceptable salt thereof according to any of [1] to [6], wherein X and Y are nitrogen and oxygen, respectively.

[8]

The compound or the pharmaceutically acceptable salt thereof according to any of [1] to [6], wherein X and Y are oxygen and nitrogen, respectively.

[9]

The compound or the pharmaceutically acceptable salt thereof according to any of [1] to [4], wherein Ar is represented by formula (Ar2).

[10]

The compound or the pharmaceutically acceptable salt thereof according to any of [1] to [4] and [9], wherein each $R^{11}$ is independently alkyl or alkoxy.

[11]

The compound or the pharmaceutically acceptable salt thereof according to any of [1] to [4], [9] and [10, wherein m is 2.

[12]

The compound or the pharmaceutically acceptable salt thereof according to [1], wherein the compound is selected from the group consisting of the following compounds:

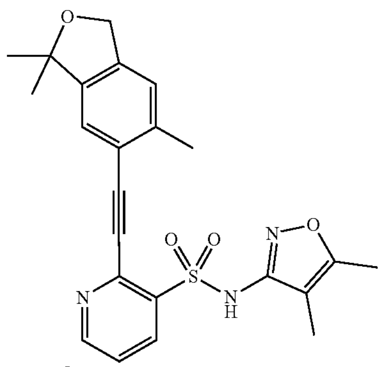

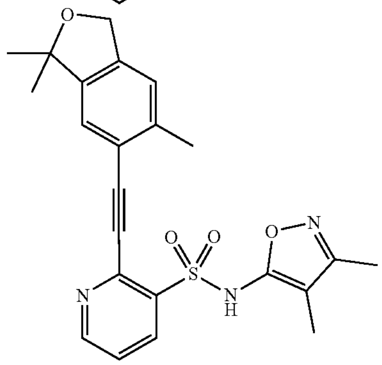

-continued
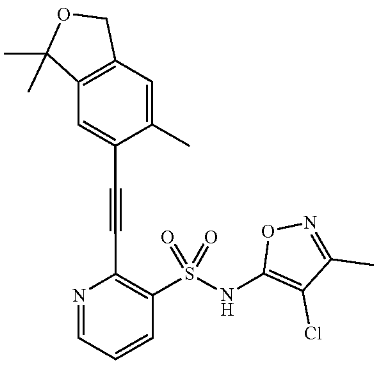
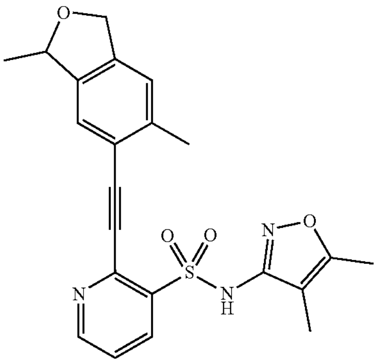
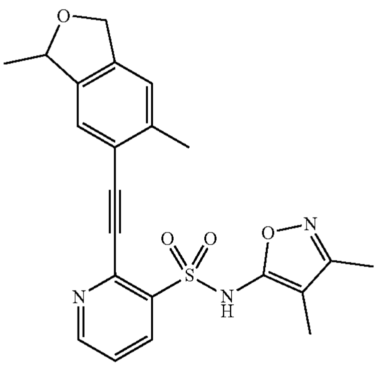
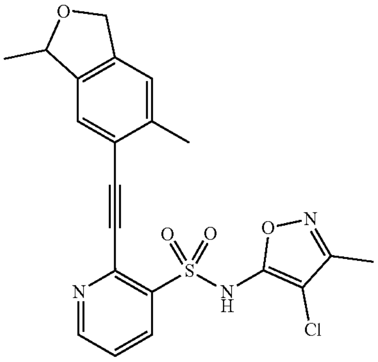
-continued
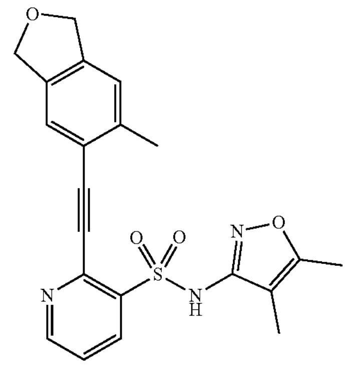
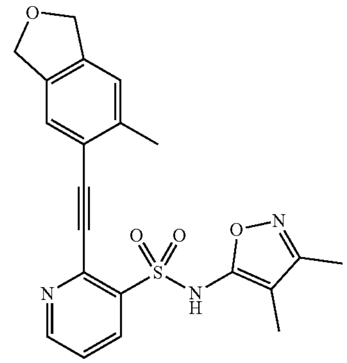
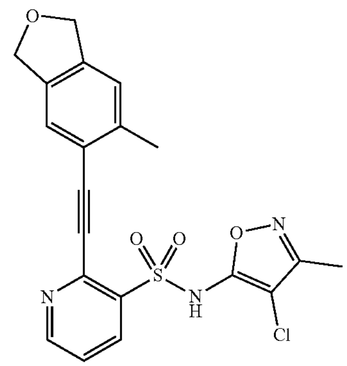
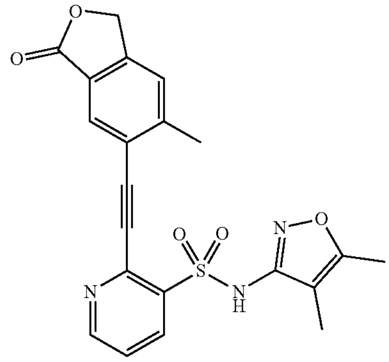

-continued
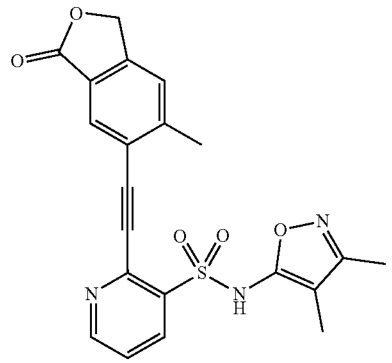
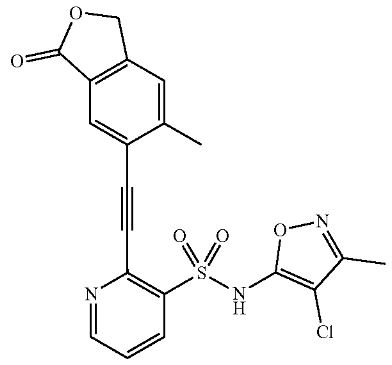
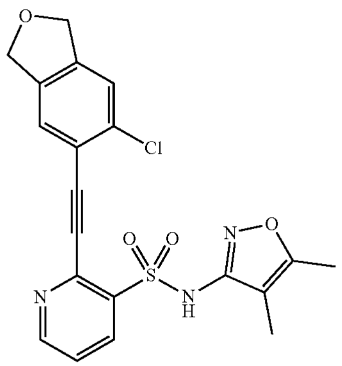
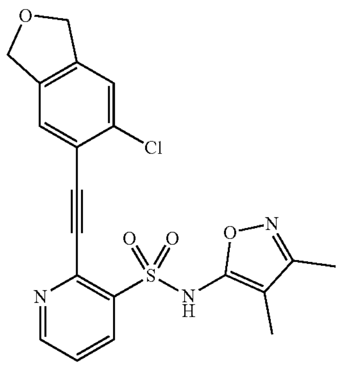
-continued
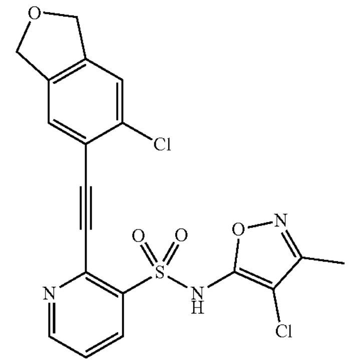
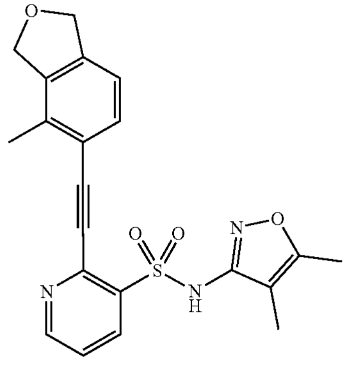
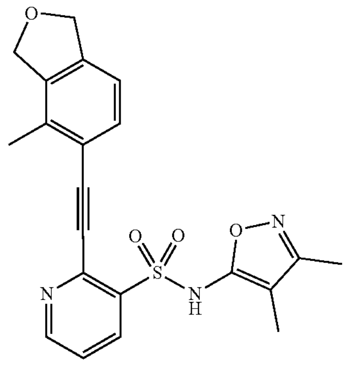
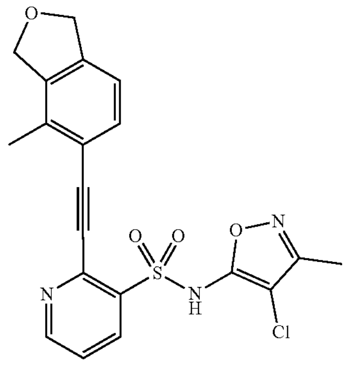

-continued
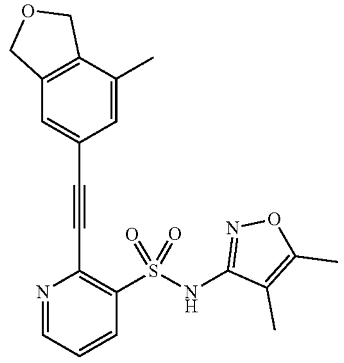
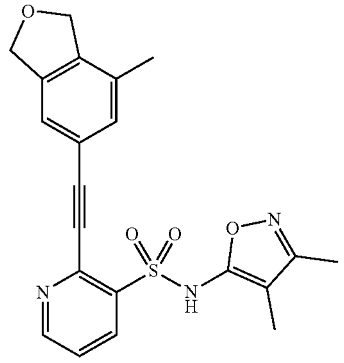
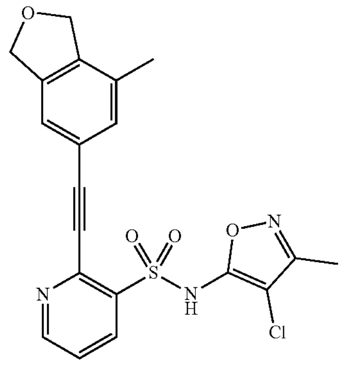
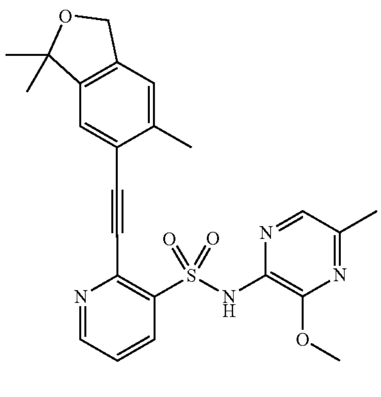
-continued
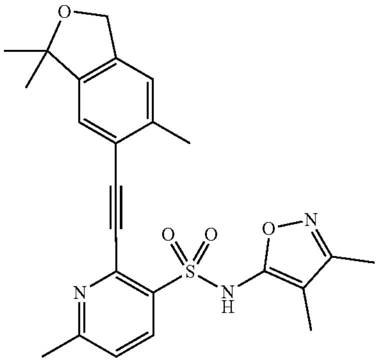
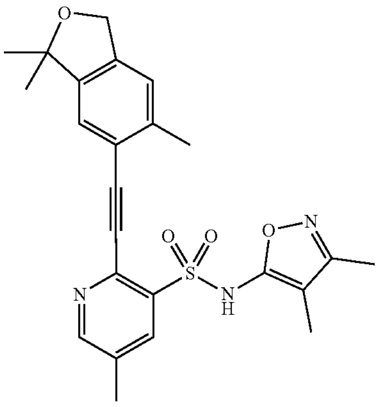
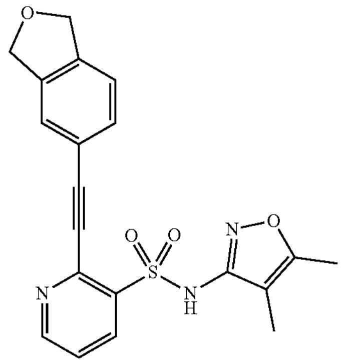
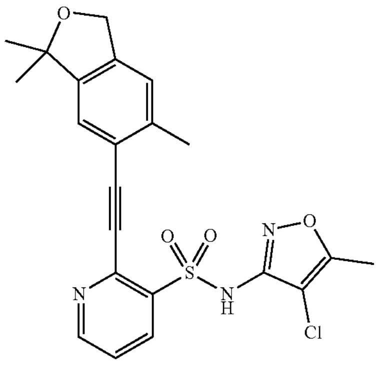

-continued

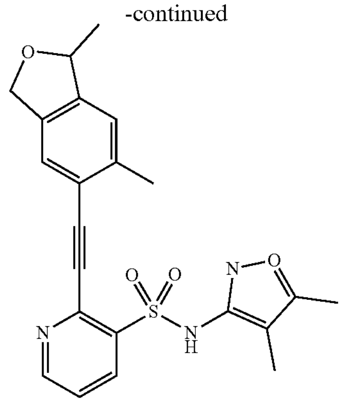

[13]

An endothelin A receptor antagonist comprising the compound or the pharmaceutically acceptable salt thereof according to any of [1] to [12].

[14]

The endothelin A receptor antagonist according to [13], wherein the endothelin A receptor antagonist selectively inhibits an endothelin A receptor in contrast to an endothelin B receptor.

[15]

A pharmaceutical composition comprising the compound or the pharmaceutically acceptable salt thereof according to any of [1] to [12].

[16]

The pharmaceutical composition according to for preventing or treating a disease selected from the group consisting of pulmonary hypertension, nephropathy, hypertension, hepatitis, cancer, pain, complications associated with autoimmune disease, heart failure, and vasospasm.

The present invention also includes the following embodiments.

[A1]

A method for inhibiting an endothelin A receptor, comprising administering an effective amount of the compound or the pharmaceutically acceptable salt thereof according to any of [1] to [12] to a patient in need thereof.

[A2]

The method according to [A1], wherein the method selectively inhibits the endothelin A receptor in contrast to an endothelin B receptor.

[A3]

A method for preventing or treating a disease, comprising administering an effective amount of the compound or the pharmaceutically acceptable salt thereof according to any of [1] to [12] to a patient in need thereof.

[A4]

The method according to [A3], wherein the disease is selected from the group consisting of pulmonary hypertension, nephropathy, hypertension, hepatitis, cancer, pain, complications associated with autoimmune disease, heart failure, and vasospasm.

[B1]

The compound or the pharmaceutically acceptable salt thereof according to any of [1] to [12] for use in the inhibition of an endothelin A receptor.

[B2]

The compound or the pharmaceutically acceptable salt thereof according to [B1], wherein the use selectively inhibits the endothelin A receptor in contrast to an endothelin B receptor.

[B3]

The compound or the pharmaceutically acceptable salt thereof according to any of [1] to [12] for use in the prevention or treatment of a disease.

[B4]

The compound or the pharmaceutically acceptable salt thereof according to [B3], wherein the disease is selected from the group consisting of pulmonary hypertension, nephropathy, hypertension, hepatitis, cancer, pain, complications associated with autoimmune disease, heart failure, and vasospasm.

[C1]

Use of the compound or the pharmaceutically acceptable salt thereof according to any of [1] to [12] for inhibiting an endothelin A receptor.

[C2]

The use according to [C1], wherein the use selectively inhibits the endothelin A receptor in contrast to an endothelin B receptor.

[C3]

Use of the compound or the pharmaceutically acceptable salt thereof according to any of [1] to [12] for preventing or treating a disease.

[C4]

The use according to [C3], wherein the disease is selected from the group consisting of pulmonary hypertension, nephropathy, hypertension, hepatitis, cancer, pain, complications associated with autoimmune disease, heart failure, and vasospasm.

[D1]

Use of the compound or the pharmaceutically acceptable salt thereof according to any of [1] to [12] in the production of an endothelin A receptor antagonist.

[D2]

The use according to [D1], wherein the endothelin A receptor antagonist selectively inhibits an endothelin A receptor in contrast to an endothelin B receptor.

[D3]

Use of the compound or the pharmaceutically acceptable salt thereof according to any of [1] to [12] in the production of a pharmaceutical composition for preventing or treating a disease.

[D4]

The use according to [D3], wherein the disease is selected from the group consisting of pulmonary hypertension, nephropathy, hypertension, hepatitis, cancer, pain, complications associated with autoimmune disease, heart failure, and vasospasm.

The present invention can provide a compound having an ETA receptor antagonistic effect, and an ETA receptor antagonist or a pharmaceutical composition comprising the compound.

DETAILED DESCRIPTION OF THE PREFERRED EMBODIMENTS

Hereinafter, the embodiments of the present invention will be specifically described. However, the present invention is not limited thereby, and various changes or modifications can be made therein without departing from the spirit of the present invention.

<Compound>

One embodiment of the present invention relates to a compound represented by the following formula (1):

(1)

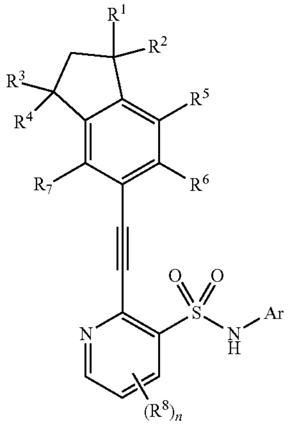

wherein $R^1$ and $R^2$ are each independently hydrogen or alkyl, $R^3$ and $R^4$ are each independently hydrogen or alkyl, or $R^3$ and $R^4$ together form oxo, $R^5$ to $R^7$ are each independently hydrogen, alkyl, haloalkyl, halogen, alkoxy or haloalkoxy, each $R^8$ is independently alkyl, haloalkyl or halogen, n is an integer of 0 to 3, and Ar is represented by the following formula (Ar1) or (Ar2):

(Ar1)

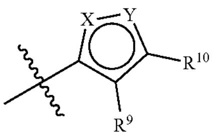

(Ar2)

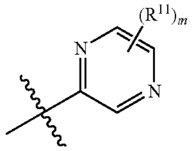

wherein

X and Y are nitrogen and oxygen, respectively, or oxygen and nitrogen, respectively, $R^9$ and $R^{10}$ are each independently hydrogen, alkyl, haloalkyl or halogen, each $R^{11}$ is independently alkyl, haloalkyl, halogen, alkoxy or haloalkoxy, and m is an integer of 0 to 3, or a pharmaceutically acceptable salt thereof.

The alkyl (including alkyl in haloalkyl; the same applies hereinafter) used herein may be linear, may be branched, or may be cyclic.

The alkyl moiety in the alkoxy (including alkoxy in haloalkoxy; the same applies hereinafter) used herein may be linear, may be branched, or may be cyclic.

The alkyl and the alkoxy used herein may each be substituted by a substituent or may be unsubstituted. Examples of the substituent include halogen as well as hydroxy, alkoxy, amino, carboxyl, and carbonyl.

In formula (1), $R^1$ and $R^2$ are each independently hydrogen or alkyl, preferably hydrogen.

The alkyl represented by each of $R^1$ and $R^2$ is preferably alkyl having 1 to 6 carbon atoms, more preferably alkyl having 1 to 3 carbon atoms, further preferably methyl.

In formula (1), $R^3$ and $R^4$ are each independently hydrogen or alkyl, or $R^3$ and $R^4$ together form oxo (=O). Preferably, $R^3$ and $R^4$ are each independently hydrogen or alkyl.

The alkyl represented by each of $R^3$ and $R^4$ is preferably alkyl having 1 to 6 carbon atoms, more preferably alkyl having 1 to 3 carbon atoms, further preferably methyl.

In formula (1), $R^5$ is hydrogen, alkyl, haloalkyl, halogen, alkoxy or haloalkoxy, preferably hydrogen.

The alkyl represented by $R^5$ is preferably alkyl having 1 to 6 carbon atoms, more preferably alkyl having 1 to 3 carbon atoms, further preferably methyl.

The alkoxy represented by $R^5$ is preferably alkoxy having 1 to 6 carbon atoms, more preferably alkoxy having 1 to 3 carbon atoms, further preferably methoxy.

The halogen or halo in the haloalkyl and the haloalkoxy represented by $R^5$ is preferably fluorine, chlorine, bromine or iodine, more preferably fluorine or chlorine.

In formula (1), $R^6$ is hydrogen, alkyl, haloalkyl, halogen, alkoxy or haloalkoxy, preferably alkyl.

The alkyl represented by $R^6$ is preferably alkyl having 1 to 6 carbon atoms, more preferably alkyl having 1 to 3 carbon atoms, further preferably methyl.

The alkoxy represented by $R^6$ is preferably alkoxy having 1 to 6 carbon atoms, more preferably alkoxy having 1 to 3 carbon atoms, further preferably methoxy.

The halogen or halo in the haloalkyl and the haloalkoxy represented by $R^6$ is preferably fluorine, chlorine, bromine or iodine, more preferably fluorine or chlorine.

In formula (1), $R^7$ is hydrogen, alkyl, haloalkyl, halogen, alkoxy or haloalkoxy, preferably hydrogen.

The alkyl represented by $R^7$ is preferably alkyl having 1 to 6 carbon atoms, more preferably alkyl having 1 to 3 carbon atoms, further preferably methyl.

The alkoxy represented by $R^7$ is preferably alkoxy having 1 to 6 carbon atoms, more preferably alkoxy having 1 to 3 carbon atoms, further preferably methoxy.

The halogen or halo in the haloalkyl and the haloalkoxy represented by $R^7$ is preferably fluorine, chlorine, bromine or iodine, more preferably fluorine or chlorine.

In formula (1), each $R^8$ is independently alkyl, haloalkyl or halogen, preferably alkyl or halogen.

The alkyl represented by $R^8$ is preferably alkyl having 1 to 6 carbon atoms, more preferably alkyl having 1 to 3 carbon atoms, further preferably methyl.

The halogen or halo in the haloalkyl represented by $R^8$ is preferably fluorine, chlorine, bromine or iodine, more preferably fluorine or chlorine.

In formula (1), n is an integer of 0 to 3, preferably 0 or 1, more preferably 0.

In formula (1), Ar is represented by formula (Ar1) or (Ar2).

In formula (Ar1), X and Y are nitrogen and oxygen, respectively, or oxygen and nitrogen, respectively.

In formula (Ar1), $R^9$ is hydrogen, alkyl, haloalkyl or halogen, preferably alkyl.

The alkyl represented by $R^9$ is preferably alkyl having 1 to 6 carbon atoms, more preferably alkyl having 1 to 3 carbon atoms, further preferably methyl.

The halogen or halo in the haloalkyl represented by $R^9$ is preferably fluorine, chlorine, bromine or iodine, more preferably fluorine or chlorine.

In formula (Ar1), $R^{10}$ is hydrogen, alkyl, haloalkyl or halogen, preferably alkyl.

The alkyl represented by $R^{10}$ is preferably alkyl having 1 to 6 carbon atoms, more preferably alkyl having 1 to 3 carbon atoms, further preferably methyl.

The halogen or halo in the haloalkyl represented by $R^{10}$ is preferably fluorine, chlorine, bromine or iodine, more preferably fluorine or chlorine.

In formula (Ar2), each $R^{11}$ is independently alkyl, haloalkyl, halogen, alkoxy or haloalkoxy, preferably alkyl or alkoxy, more preferably alkyl and alkoxy.

The alkyl represented by $R^{11}$ is preferably alkyl having 1 to 6 carbon atoms, more preferably alkyl having 1 to 3 carbon atoms, further preferably methyl.

The alkoxy represented by $R^{11}$ is preferably alkoxy having 1 to 6 carbon atoms, more preferably alkoxy having 1 to 3 carbon atoms, further preferably methoxy.

The halogen or halo in the haloalkyl and the haloalkoxy represented by $R^{11}$ is preferably fluorine, chlorine, bromine or iodine, more preferably fluorine or chlorine.

In formula (Ar2), m is an integer of 0 to 3, preferably 2.

The compound represented by formula (1) is not particularly limited and is preferably any of the following compounds.

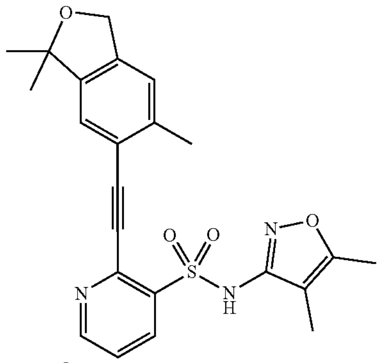

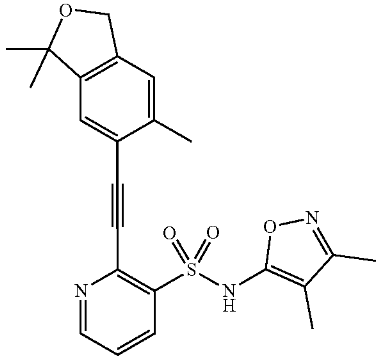

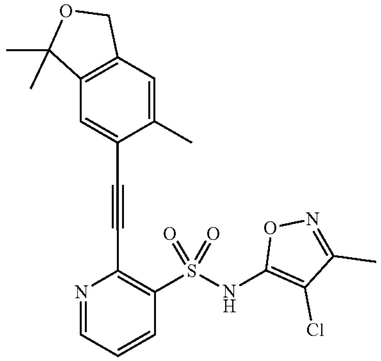

-continued

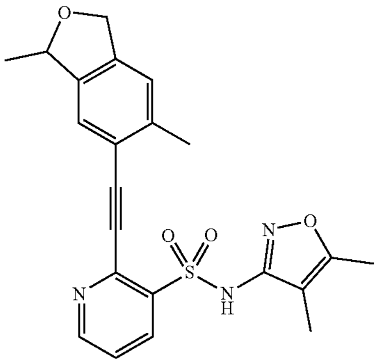

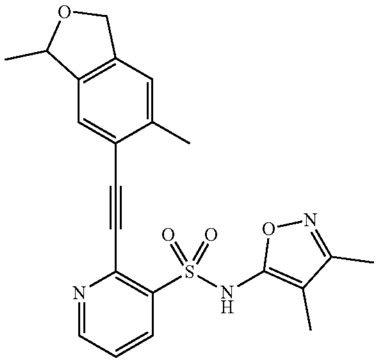

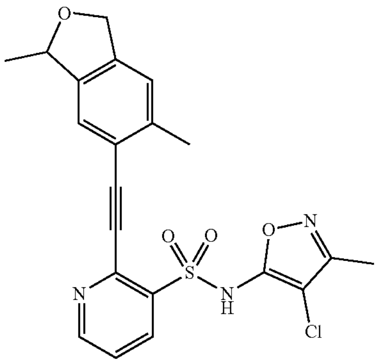

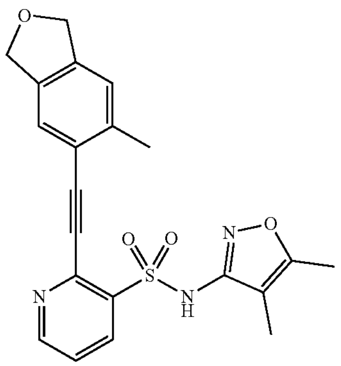

-continued
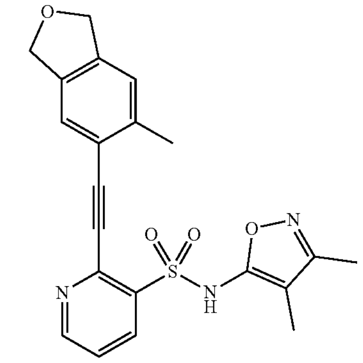
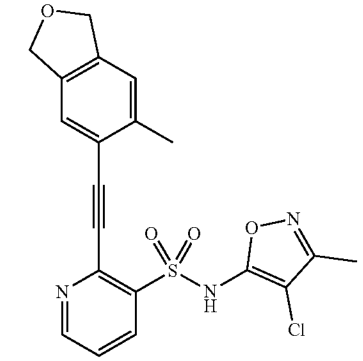
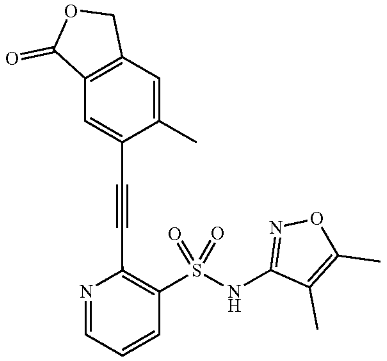
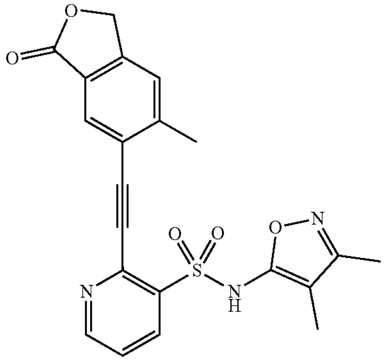
-continued
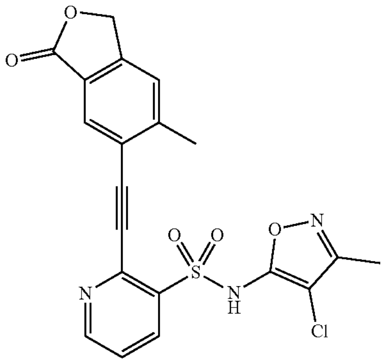
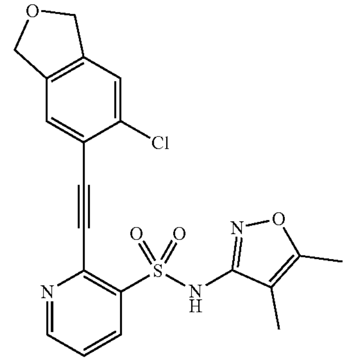
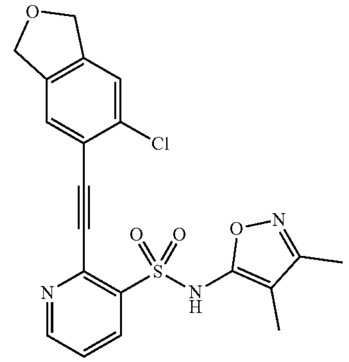
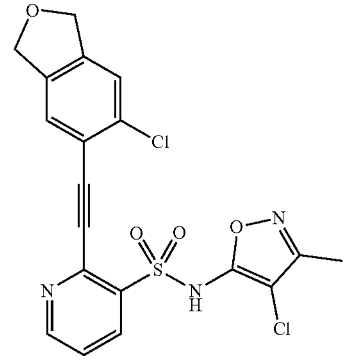

-continued
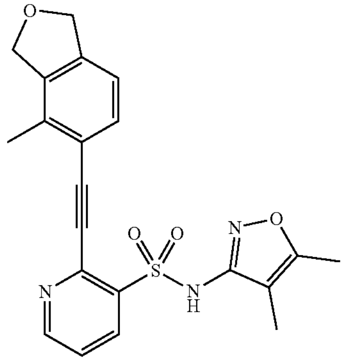
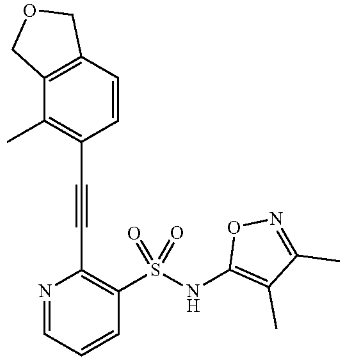
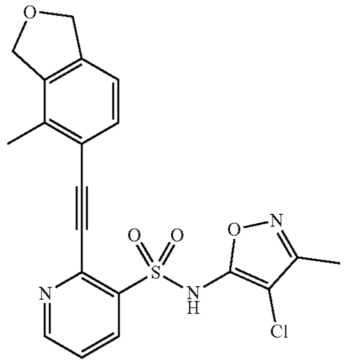
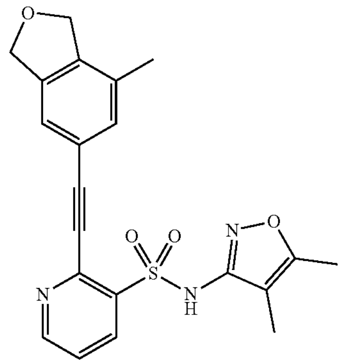
-continued
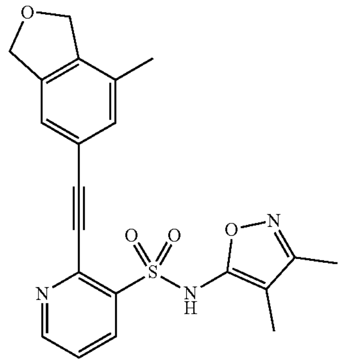
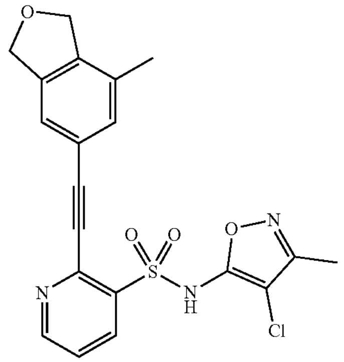
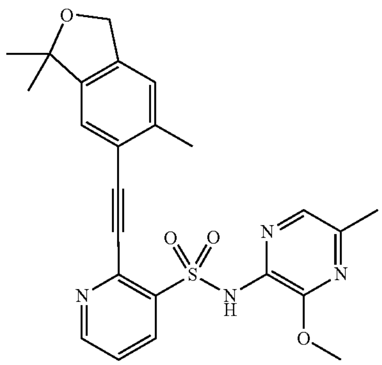
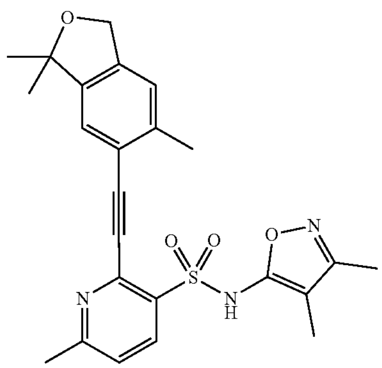

-continued

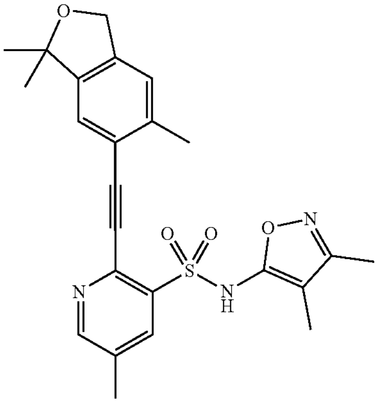

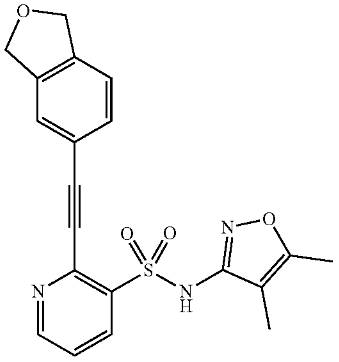

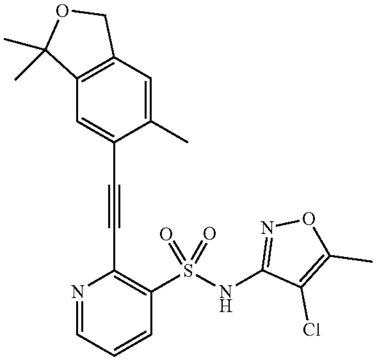

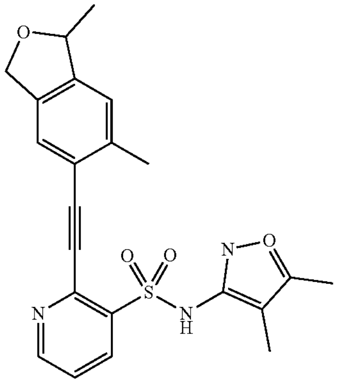

The pharmaceutically acceptable salt of the compound represented by formula (1) is not particularly limited as long as the salt can be used as a medicament. Examples thereof can include: inorganic acid salts such as hydrochloride, sulfate, nitrate, phosphate, and hydrobromide; organic acid salts such as fumarate, maleate, malate, tartrate, succinate, citrate, methanesulfonate, p-toluenesulfonate, acetate, lactate, and palmitate; alkali metal salts; and alkaline earth metal salts.

The compound represented by formula (1) or the pharmaceutically acceptable salt thereof may form a solvate such as a hydrate. The solvate used herein is encompassed by the compound represented by formula (1) or the pharmaceutically acceptable salt thereof.

When the compound represented by formula (1) or the pharmaceutically acceptable salt thereof has stereoisomers (e.g., enantiomers and diastereomers), the individual stereoisomers and a mixture thereof (e.g., a racemate) are encompassed by the compound represented by formula (1) or the pharmaceutically acceptable salt thereof.

The form of the compound represented by formula (1) or the pharmaceutically acceptable salt thereof is not particularly limited. The compound represented by formula (1) or the pharmaceutically acceptable salt thereof may be in the form of crystals or may be in an amorphous form. When the compound represented by formula (1) or the pharmaceutically acceptable salt thereof has crystal polymorphs, the compound represented by formula (1) or the pharmaceutically acceptable salt thereof may be in any crystal form.

<Endothelin a Receptor Antagonist>

One embodiment of the present invention relates to an ETA receptor antagonist comprising the compound represented by formula (1) or the pharmaceutically acceptable salt thereof. An ETA receptor and an ETB receptor are known as endothelin receptors. The inhibition of the ETB receptor may cause problems such as the elevation of endothelin levels in blood or the occurrence of peripheral edema. Preferably, the ETA receptor antagonist of the present embodiment can selectively inhibit the endothelin A receptor in contrast to the endothelin B receptor.

Specifically, ETB receptor inhibitory concentration ($IC_{50}$)/ETA receptor inhibitory concentration ($IC_{50}$) is preferably 2,000 or higher, more preferably 4,000 or higher, further preferably 6,000 or higher, still further preferably 8,000 or higher, particularly preferably 10,000 or higher. The upper limit of ETB receptor inhibitory concentration ($IC_{50}$)/ETA receptor inhibitory concentration ($IC_{50}$) is not particularly limited and may be, for example, 100,000, 80,000, 60,000, or 40,000. The ETB receptor inhibitory concentration and the ETA receptor inhibitory concentration can be measured by a method described in Examples.

The ETA receptor inhibitory concentration ($IC_{50}$) of the ETA receptor antagonist of the present embodiment is preferably 10 nM or lower, more preferably 8.0 nM or lower, further preferably 6.0 nM or lower, still further preferably 4.0 nM or lower, particularly preferably 2.0 nM or lower. The lower limit of the ETA receptor inhibitory concentration ($IC_{50}$) is not particularly limited and may be, for example, 0.005 nM, 0.01 nM, or 0.05 nM.

The ETB receptor inhibitory concentration ($IC_{50}$) of the ETA receptor antagonist of the present embodiment is preferably 1,000 nM or higher, more preferably 2,000 nM or higher, further preferably 3,000 nM or higher, still further preferably 4,000 nM or higher, particularly preferably 5,000 nM or higher. The upper limit of the ETB receptor inhibitory concentration ($IC_{50}$) is not particularly limited and may be, for example, 10,000 nM, 15,000 nM, or 20,000 nM.

Use of the ETA receptor antagonist of the present embodiment can treat and/or prevent a disease related to (mediated by) an ETA receptor.

<Pharmaceutical Composition>

One embodiment of the present invention relates to a pharmaceutical composition comprising the compound represented by formula (1) or the pharmaceutically acceptable salt thereof.

Examples of the disease targeted by the pharmaceutical composition of the present embodiment can include pulmonary hypertension, nephropathy, hypertension, hepatitis, cancer, pain, complications associated with autoimmune disease, heart failure, and vasospasm.

Examples of the nephropathy can include focal segmental glomerulosclerosis, IgA nephropathy, chronic kidney disease (including diabetic nephropathy), and renal damage associated with sickle cell syndrome.

Examples of the hepatitis can include non-alcoholic steatohepatitis (NASH) and alcoholic hepatitis.

Examples of the cancer can include prostate cancer, squamous cell cancer, non-small cell lung cancer, and melanoma.

Examples of the pain can include pain associated with endometriosis, chronic pain, neuropathic pain, cancer pain, and inflammatory pain.

Examples of the complications associated with autoimmune disease can include complications associated with scleroderma, and complications associated with vasculitis.

Examples of the heart failure can include right heart failure, left heart failure, heart failure associated with hypertrophic cardiomyopathy, heart failure associated with dilated cardiomyopathy, heart failure with preserved ejection fraction, and heart failure with reduced ejection fraction.

Examples of the vasospasm can include cerebral vasospasm and vasospastic angina.

The pharmaceutical composition of the present embodiment can be administered orally or parenterally. Examples of the dosage form for oral administration include tablets, pills, granules, powders, capsules, syrups, emulsions, and suspensions. Examples of the dosage form for parenteral administration include injections, infusions, drops, eye drops and suppositories.

The pharmaceutical composition of the present embodiment may optionally contain an excipient, a binder, a lubricant, a disintegrant, a sweetener, a surfactant, a suspending agent, an emulsifying agent, a colorant, a preservative, a fragrance, a corrigent, a stabilizer, a thickener, and the like.

The dose of the pharmaceutical composition of the present embodiment varies depending on the state or body weight of a patient, the type of the compound, the type of the disease, an administration route, etc., and a proper amount can be determined by a physician.

<Method for Producing Compound>

The compound represented by formula (1) or the pharmaceutically acceptable salt thereof can be synthesized by appropriate use of a method known in the art. Examples of the synthesis method can include the following schemes A to C:

<Scheme A>

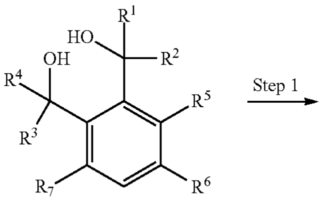

(1)

-continued

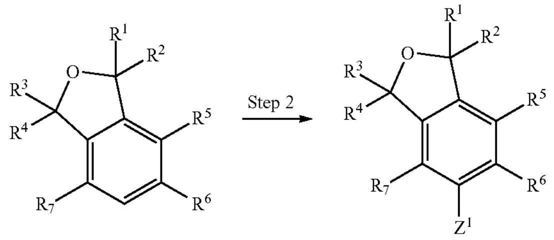

(2) (3)

<Scheme B>

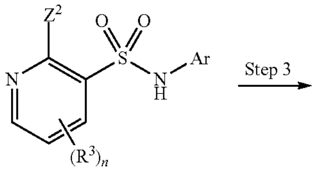

(4)

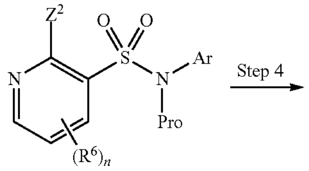

(5)

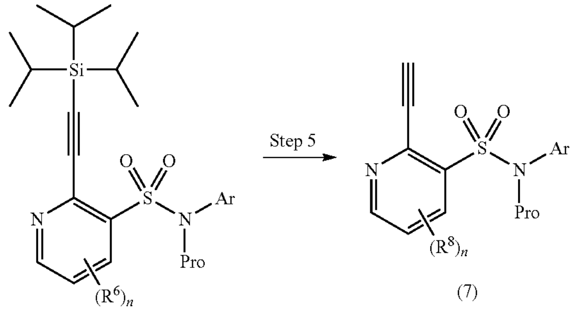

(6) (7)

<Scheme C>

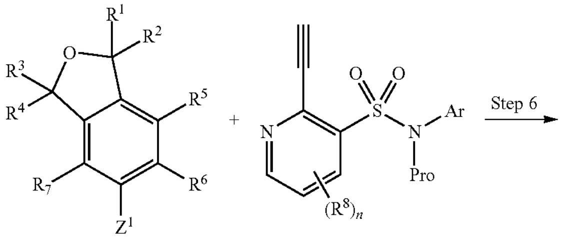

(3) (7)

-continued

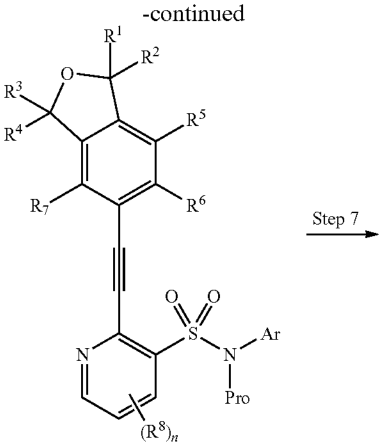

(8)

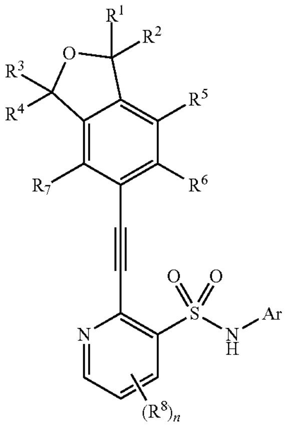

(9)

In schemes A to C, $R^1$ to $R^8$, n and Ar are as defined above, $Z^1$ and $Z^2$ each represent halogen, and Pro represents a protective group.

In scheme A, compound (1) is reacted with, for example, sodium hydride, to obtain compound (2) (step 1). Compound (2) is reacted with halogen (e.g., iodine) to obtain compound (3) (step 2).

In scheme B, the amino group of compound (4) is protected with a protective group (e.g., a methoxymethyl group) to obtain compound (5) (step 3). Compound (5) is reacted with triisopropylsilylacetylene to obtain compound (6) (step 4). Compound (6) is reacted with, for example, tetrabutylammonium fluoride, to obtain compound (7) (step 5).

In scheme C, compound (3) is reacted with compound (7) to obtain compound (8) (step 6). Compound (8) is deprotected to obtain compound (9) (step 7).

When the compound represented by formula (1) or the pharmaceutically acceptable salt thereof has stereoisomers, the isomers can be resolved into each one by a method known in the art. Examples of the method known in the art can include chromatography, enzymatic methods, and crystallization methods.

EXAMPLES

Hereinafter, the present invention will be described in more detail with reference to Examples and Comparative Examples. However, the technical scope of the present invention is not limited thereto.

Production Example 1-1

6-Bromo-5-methylisobenzofuran-1 (3H)-one

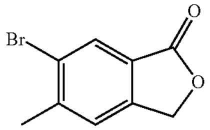

To a mixture of 3-bromo-4-methylbenzoic acid (1.5 g, 7.01 mmol) and 1,1-dibromomethane (20 mL), dipotassium hydrogen phosphate (3.6 g, 21.0 mmol) and palladium(II) acetate (157 mg, 0.70 mmol) were added at room temperature, and the reaction mixture was stirred at 140° C. for 48 hours. The reaction mixture was brought back to room temperature, and filtered through celite while washed with ethyl acetate. The solvent in the filtrate was distilled off under reduced pressure, and the residue was triturated with ethanol to obtain the title compound (1.3 g).

1H NMR (400 MHZ, CDCl3): δ 8.09 (s, 1H), 7.37 (s, 1H), 5.23 (s, 2H), 2.53 (s, 3H).

Production Example 1-2

6-Bromo-1,1,5-trimethyl-1,3-dihydroisobenzofuran

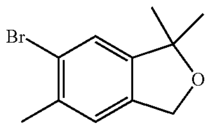

To a mixture of 6-bromo-5-methylisobenzofuran-1 (3H)-one (1.00 g, 4.41 mmol) and tetrahydrofuran (10 mL), methyl magnesium iodide (3.0 M solution in diethyl ether, 4.5 mL, 13.5 mmol) was added at −15° C., and the mixture was stirred at the same temperature as above for 2 hours. Ice-cold water was added to the reaction mixture, followed by extraction with ethyl acetate. The organic layer was washed with saturated saline and dried over sodium sulfate, and the solvent was distilled off under reduced pressure. The residue was purified by silica gel column chromatography (hexane/ethyl acetate) to obtain the title compound (615 mg).

1H NMR (400 MHZ, CDCl3): δ 7.45 (d, J=5.2 Hz, 1H), 7.20 (d, J=5.2 Hz, 1H), 4.77 (d, J=5.2 Hz, 2H), 2.37 (d, J=5.2 Hz, 3H), 1.68 (d, J=5.2 Hz, 6H).

Production Example 1-3

2-Chloro-N-(4,5-dimethylisoxazol-3-yl)pyridine-3-sulfonamide

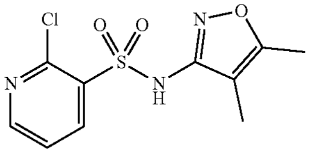 [SMILES: Cc1onc(NS(=O)(=O)c2cccnc2Cl)c1C]

To a mixture of 4,5-dimethylisoxazol-3-amine (1.0 g, 8.92 mmol) and pyridine (20.0 mL), 4-dimethylaminopyridine (109 mg, 0.892 mmol) and 2-chloropyridine-3-sulfonyl chloride (2.84 g, 13.4 mmol) were gradually added at 0° C., and the reaction mixture was stirred at 50° C. for 16 hours. Ice-cold water was added to the reaction mixture, followed by extraction with ethyl acetate. The organic layer was washed with saturated saline and dried over sodium sulfate. The solvent was distilled off under reduced pressure to obtain the title compound (1.50 g) in a crude form. This compound was used in the next reaction without being further purified.

ESI-MS: m/z 288.0 [M+1]+

Production Example 1-4

2-Chloro-N-(4,5-dimethylisoxazol-3-yl)-N-(methoxymethyl)pyridine-3-sulfonamide

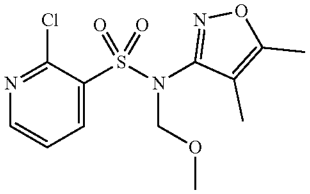 [SMILES: COCN(c1noc(C)c1C)S(=O)(=O)c1cccnc1Cl]

To a mixture of 2-chloro-N-(4,5-dimethylisoxazol-3-yl) pyridine-3-sulfonamide (1.80 g, 6.26 mmol) and DMF (30.0 mL), 60% sodium hydride (695 mg, 17.4 mmol) was gradually added at 0° C., and the mixture was stirred at the same temperature as above for 30 minutes. Chloromethyl methyl ether (1.06 mL, 13.9 mmol) was gradually added to the reaction mixture, and the mixture was stirred at room temperature for 3 hours. Ice-cold water was added to the reaction mixture, followed by extraction with ethyl acetate. The organic layer was washed with saturated saline and dried over sodium sulfate, and the solvent was distilled off under reduced pressure. The residue was purified by silica gel column chromatography (hexane/ethyl acetate) to obtain the title compound (1.20 g).

ESI-MS: m/z 332.07 [M+1]+

Production Example 1-5

N-(4,5-Dimethylisoxazol-3-yl)-N-(methoxymethyl)-2-((triisopropylsilyl)ethynyl)pyridine-3-sulfonamide

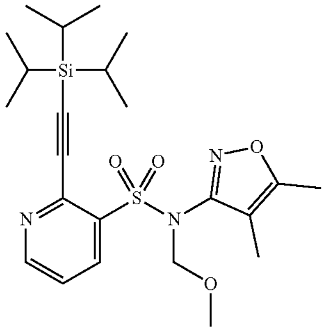 [SMILES: COCN(c1noc(C)c1C)S(=O)(=O)c1cccnc1C#C[Si](C(C)C)(C(C)C)C(C)C]

In an argon atmosphere, to a mixture of 2-chloro-N-(4,5-dimethylisoxazol-3-yl)-N-(methoxymethyl)pyridine-3-sulfonamide (400 mg, 1.21 mmol), triethylamine (0.50 mL, 3.62 mmol), triisopropylsilylacetylene (440 mg, 2.41 mmol) and THF (5.00 mL), bis(triphenylphosphine)palladium(II) dichloride (84.6 mg, 0.121 mmol) and copper(I) iodide (11.5 mg, 0.0362 mmol) were added, and the reaction mixture was stirred at 55° C. for 6 hours. Ice-cold water was added to the reaction mixture, followed by extraction with ethyl acetate. The organic layer was washed with saturated saline and dried over sodium sulfate, and the solvent was distilled off under reduced pressure. The residue was purified by silica gel column chromatography (hexane/ethyl acetate) to obtain the title compound (0.150 g).

1H NMR (400 MHZ, DMSO-$d_6$) δ 8.82 (d, 1H, J=4.8 Hz), 8.21 (d, 1H, J=8 Hz), 7.63-7.60 (m, 1H), 5.16 (s, 2H), 3.34 (s, 3H), 2.32 (s, 3H), 1.85 (s, 3H), 1.14 (bs, 21H).

Production Example 1-6

N-(4,5-Dimethylisoxazol-3-yl)-2-ethynyl-N-(methoxymethyl)pyridine-3-sulfonamide

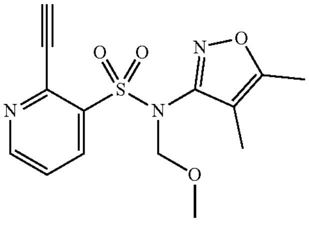 [SMILES: C#Cc1ncccc1S(=O)(=O)N(COC)c1noc(C)c1C]

To a mixture of N-(4,5-dimethylisoxazol-3-yl)-N-(methoxymethyl)-2-((triisopropylsilyl)ethynyl)pyridine-3-sulfonamide (150 mg, 4.3 mmol) and THF (3.00 mL), tetrabutylammonium fluoride (1 mol/L solution in tetrahydrofuran, 0.942 mL, 12.9 mmol) was gradually added at 0° C., and the reaction mixture was stirred at room temperature for 2 hours. Ice-cold water was added to the reaction mixture, followed by extraction with ethyl acetate. The organic layer was washed with saturated saline and dried over sodium sulfate, and the solvent was distilled off under reduced pressure. The residue was purified by silica gel column chromatography (hexane/ethyl acetate) to obtain the title compound (0.060 g).

ESI-MS: m/z 322.19 [M+1]+

Production Example 1-7

N-(4,5-Dimethylisoxazol-3-yl)-N-(methoxymethyl)-2-((3,3,6-trimethyl-1,3-dihydroisobenzofuran-5-yl)ethynyl)pyridine-3-sulfonamide

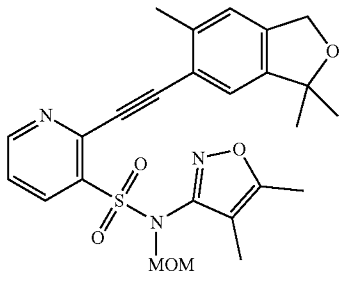

In an argon atmosphere, to a mixture of N-(4,5-dimethylisoxazol-3-yl)-2-ethynyl-N-(methoxymethyl)pyridine-3-sulfonamide (0.4 g, 1.25 mmol) and N, N-dimethylformamide (5 mL), 6-bromo-1,1,5-trimethyl-1,3-dihydroisobenzofuran (0.36 g, 1.49 mmol), copper (II) sulfate (7.8 mg, 0.04 mmol), triethylamine (1.04 mL, 7.48 mmol), sodium ascorbate (24 mg, 0.12 mmol) and tetrakis (triphenylphosphine)palladium(0) (28 mg, 0.02 mmol) were added, and the reaction mixture was stirred at 80° C. for 4 hours. The reaction mixture was brought back to room temperature, and ice-cold water was added thereto, followed by extraction with ethyl acetate. The organic layer was washed with saturated saline and dried over sodium sulfate, and the solvent was distilled off under reduced pressure. The residue was purified by high-performance liquid chromatography (Kinetex F5, (250×50 mm) 5 μm, 0.1% aqueous trifluoroacetic acid solution/acetonitrile-methanol (1:1) mixed solution) to obtain the title compound (615 mg).

ESI-MS: m/z 482.29 [M+1]+

Example 1

N-(4,5-Dimethylisoxazol-3-yl)-2-((3,3,6-trimethyl-1,3-dihydroisobenzofuran-5-yl)ethynyl)pyridine-3-sulfonamide

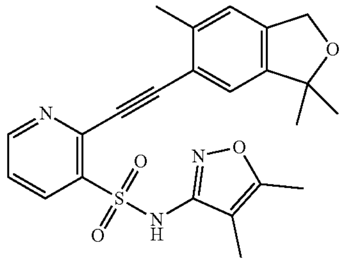 [SMILES: Cc1cc2c(cc1C#Cc1ncccc1S(=O)(=O)Nc1noc(C)c1C)C(C)(C)OC2]

To a mixture of N-(4,5-dimethylisoxazol-3-yl)-N-(methoxymethyl)-2-((3,3,6-trimethyl-1,3-dihydroisobenzofuran-5-yl)ethynyl)pyridine-3-sulfonamide (90 mg, 0.18 mmol) and methanol (5 mL), 6 mol/L hydrochloric acid (1 mL) was added at 0° C., and the reaction mixture was stirred at 50° C. for 4 hours. The reaction mixture was brought back to room temperature, and ice-cold water was added thereto, followed by extraction with ethyl acetate. The organic layer was washed with saturated saline and dried over sodium sulfate, and the solvent was distilled off under reduced pressure. The residue was purified by high-performance liquid chromatography (Omega Ps C18 (250×21.2 mm) 5 μm, 0.1% aqueous trifluoroacetic acid solution/acetonitrile-methanol (1:1) mixed solution) to obtain the title compound (30 mg).

ESI-MS: m/z 438.24 [M+1]+

1H NMR (400 MHZ, DMSO-d6): δ 11.06 (s, 1H), 8.83 (d, J=4.8 Hz, 2H), 8.35 (d, J=8 Hz, 1H), 7.66-7.63 (m, 1H), 7.48 (s, 1H), 7.24 (s, 1H), 4.96 (s, 2H), 2.46 (s, 3H), 2.07 (s, 3H), 1.81 (s, 3H), 1.43 (s, 6H).

Production Example 2-1

(E)-N'-(2-Hydroxy-5-methylbenzylidene)acetohydrazide

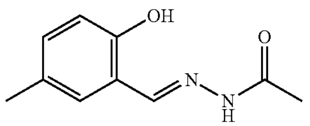

To a mixture of 2-hydroxy-5-methylbenzaldehyde (10 g, 73.5 mmol) and ethanol (50 mL), acetohydrazide (5.44 g, 73.5 mmol) was gradually added at room temperature, and the reaction mixture was stirred at 90° C. for 16 hours. The solvent in the reaction mixture was distilled off under reduced pressure, and the residue was washed with hexane to obtain the title compound (10 g) in a crude form. This compound was used in the next reaction without being further purified.

Production Example 2-2

2-Acetyl-5-methylbenzaldehyde

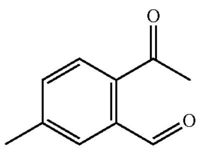

To a mixture of (E)-N'-(2-hydroxy-5-methylbenzylidene) acetohydrazide (6 g, 31.3 mmol) and tetrahydrofuran (90 mL), lead(IV) acetate (15.1 g, 34.4 mmol) was added at 0° C., and the reaction mixture was stirred at room temperature for 16 hours. The reaction mixture was filtered through celite while washed with ethyl acetate. The filtrate was washed with a saturated aqueous solution of sodium bicarbonate and saturated saline and dried over sodium sulfate, and the solvent was distilled off under reduced pressure. The residue was purified by silica gel column chromatography (hexane/ethyl acetate) to obtain the title compound (1.3 g).

ESI-MS: m/z 163.1 [M+1]+

Production Example 2-3

1-(2-(Hydroxymethyl)-4-methylphenyl)ethan-1-ol

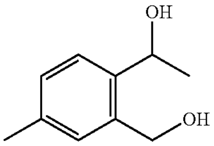

To a mixture of 2-acetyl-5-methylbenzaldehyde (2.5 g, 15.4 mmol), tetrahydrofuran (10 mL) and ethanol (30 mL), sodium borohydride (2.9 g, 77.2 mmol) was added at 0° C., and the reaction mixture was stirred at 70° C. for 2 hours. The reaction mixture was brought back to room temperature, and ice-cold water was added to the reaction mixture, followed by extraction with ethyl acetate. The organic layer was washed with a saturated aqueous solution of sodium bicarbonate and saturated saline and dried over sodium sulfate, and the solvent was distilled off under reduced pressure. The residue was purified by silica gel column chromatography (hexane/ethyl acetate) to obtain the title compound (1.8 g).

1H NMR (400 MHZ, CDCl3): δ 7.38-7.35 (m, 1H), 7.16 (d, J=2.4 Hz, 2H), 5.19-5.14 (m, 1H), 4.81 (t, J=8 Hz, 1H), 4.63 (d, J=12 Hz, 2H), 2.68 (s, 2H), 2.35 (d, J=4.8 Hz, 3H), 2.45 (d, J=5.2 Hz, 2H).

Production Example 2-4

1,5-Dimethyl-1,3-dihydroisobenzofuran

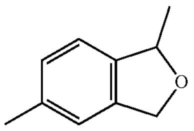

To a mixture of 1-(2-(hydroxymethyl)-4-methylphenyl) ethan-1-ol (1.6 g, 9.64 mmol) and tetrahydrofuran (16 mL), 60% sodium hydride (1.07 g, 11.2 mmol) was gradually added at 0° C., and the mixture was stirred at the same temperature as above for 30 minutes. Trimethyl phosphate (3.5 g, 24.1 mmol) was added to the reaction mixture at room temperature, and the mixture was stirred at the same temperature as above for 16 hours. Water was added to the reaction mixture, followed by extraction with ethyl acetate. The organic layer was washed with saturated saline and dried over sodium sulfate, and the solvent was distilled off under reduced pressure. The residue was purified by silica gel column chromatography (hexane/ethyl acetate) to obtain the title compound (1.0 g).

1H NMR (400 MHZ, CDCl3): δ 7.12-7.06 (m, 3H), 5.31 (d, J=6.4 Hz, 1H), 5.14-5.01 (m, 2H), 2.39 (s, 3H), 1.50 (d, J=6.4 Hz, 3H).

Production Example 2-5

6-Bromo-1,5-dimethyl-1,3-dihydroisobenzofuran

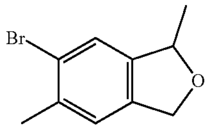

To a mixture of 1,5-dimethyl-1,3-dihydroisobenzofuran (700 mg, 4.73 mmol) and dichloromethane (7 mL), N-bromosuccinimide (842 mg, 4.73 mmol) and trifluoromethanesulfonic acid (700 mg, 4.73 mmol) were added at 0° C., and the mixture was stirred at room temperature for 2 hours. Ice-cold water was added to the reaction mixture, followed by extraction with ethyl acetate. The organic layer was washed with saturated saline and dried over sodium sulfate, and the solvent was distilled off under reduced pressure. The residue was purified by silica gel column chromatography (hexane/ethyl acetate) to obtain the title compound (0.7 g).

1H NMR (400 MHZ, CDCl3): δ 7.32 (dd, J=8.4 Hz, J=9.2 Hz, 1H), 7.09 (d, J=8 Hz, 1H), 5.29-5.24 (m, 1H), 5.07-5.02 (m, 1H), 4.95 (t, J=7.6 Hz, 1H), 2.41 (d, J=8.4 Hz, 3H), 1.49-1.46 (m, 3H).

Production Example 2-6

2-((3,6-Dimethyl-1,3-dihydroisobenzofuran-5-yl) ethynyl)-N-(4,5-dimethylisoxazol-3-yl)-N-(methoxymethyl)pyridine-3-sulfonamide

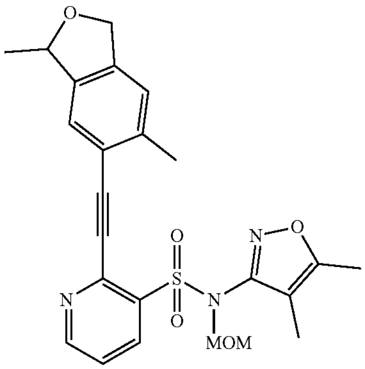

In an argon atmosphere, to a mixture of N-(4,5-dimethylisoxazol-3-yl)-2-ethynyl-N-(methoxymethyl)pyridine-3-sulfonamide (0.7 g, 2.18 mmol) and N, N-dimethylformamide (5 mL), 6-bromo-1,5-dimethyl-1,3-dihydroisobenzofuran (0.54 g, 2.40 mmol), copper(I) iodide (83 mg, 0.436 mmol), triethylamine (0.6 mL, 4.36 mmol) and tetrakis(triphenylphosphine)palladium(0) (250 mg, 0.218 mmol) were added, and the reaction mixture was stirred at 80° C. for 4 hours. The reaction mixture was brought back to room temperature, and ice-cold water was added thereto, followed by extraction with ethyl acetate. The organic layer was washed with saturated saline and dried over sodium sulfate, and the solvent was distilled off under reduced pressure. The residue was purified by high-performance liquid chromatography (Luna C8 (250×50 mm) 10

μm, 0.1% aqueous formic acid solution/acetonitrile) to obtain the title compound (50 mg).

ESI-MS: m/z 468.27 [M+1]+

Example 2

2-((3,6-Dimethyl-1,3-dihydroisobenzofuran-5-yl) ethynyl)-N-(4,5-dimethylisoxazol-3-yl)pyridine-3-sulfonamide

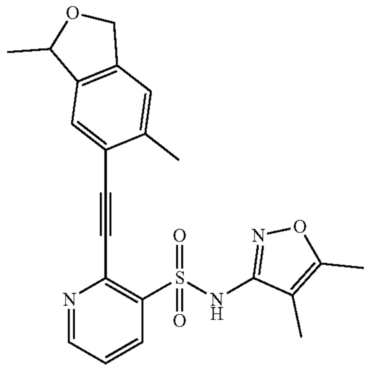

To a mixture of 2-((3,6-dimethyl-1,3-dihydroisobenzofuran-5-yl)ethynyl)-N-(4,5-dimethylisoxazol-3-yl)-N-(methoxymethyl)pyridine-3-sulfonamide (50 mg, 0.107 mmol) and methanol (5 mL), 6 mol/L hydrochloric acid (1 mL) was added at 0° C., and the reaction mixture was stirred at 50° C. for 4 hours. The reaction mixture was brought back to room temperature, and ice-cold water was added thereto, followed by extraction with ethyl acetate. The organic layer was washed with saturated saline and dried over sodium sulfate, and the solvent was distilled off under reduced pressure. The residue was purified by high-performance liquid chromatography (Luna C8 (250×50 mm) 10 μm, 0.1% aqueous formic acid solution/acetonitrile) to obtain the title compound (22 mg).

ESI-MS: m/z 424.31 [M+1]+

1H NMR (400 MHZ, DMSO-d6): δ 11.06 (s, 1H), 8.82 (d, J=4 Hz, 1H), 8.34 (t, J=6.8 Hz, 1H), 7.66-7.62 (m, 1H), 7.47 (d, J=5.2 Hz, 1H), 7.27 (d, J=5.2 Hz, 1H), 5.22 (d, J=9.6 Hz, 1H), 5.05-5.00 (m, 1H), 4.95-4.90 (m, 1H), 2.47 (s, 3H), 2.09 (d, J=4.8 Hz, 3H), 1.81 (d, J=4.8 Hz, 3H), 1.42 (t, J=5.2 Hz, 3H).

Production Example 3-1

(4-Methyl-1,2-phenylene)dimethanol

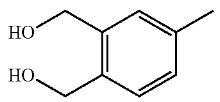

To a mixture of 5-methylisobenzofuran-1,3-dione (100 g, 617 mmol) and THF (1000 mL), borane dimethylsulfide (156 mL, 1.85 mol) was gradually added at 0° C., and the reaction mixture was stirred at 80° C. for 16 hours. The reaction mixture was brought back to room temperature, and methanol was added to the reaction mixture. The solvent was distilled off under reduced pressure. The residue was purified by silica gel column chromatography (hexane/ethyl acetate) to obtain the title compound (40.0 g).

1H NMR (400 MHZ, DMSO-d6) δ 7.23 (d, 1H, J=8.0 Hz), 7.18 (br s, 1H), 7.02 (d, 1H, J=7.6 Hz), 5.02 (t, 1H, J=5.6 Hz), 4.98 (t, 1H, J=5.2 Hz), 4.49 (dd, 4H, J=8.4, 14 Hz), 2.27 (s, 3H).

Production Example 3-2

5-Methyl-1,3-dihydroisobenzofuran

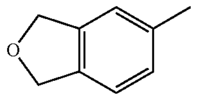

To a mixture of (4-methyl-1,2-phenylene)dimethanol (40.0 g, 263 mmol) and DMF (200 mL), 50% sodium hydride (15.8 g, 657 mmol) was gradually added at 0° C., and the mixture was stirred at the same temperature as above for 30 minutes. Trimethyl phosphate (92.0 g, 657 mmol) was gradually added to the reaction mixture, and the mixture was stirred at room temperature for 3 hours. Ice-cold water was added to the reaction mixture, followed by extraction with ethyl acetate. The organic layer was washed with saturated saline and dried over sodium sulfate, and the solvent was distilled off under reduced pressure. The residue was purified by silica gel column chromatography (hexane/ethyl acetate) to obtain the title compound (20.50 g).

1H NMR (400 MHZ, $CDCl_3$) δ 7.12 (d, 1H, J=7.6 Hz), 7.08 (br s, 1H), 7.06 (d, 1H, J=4.8 Hz), 5.08 (s, 4H), 2.37 (s, 3H).

Production Example 3-3

5-Iodo-6-methyl-1,3-dihydroisobenzofuran

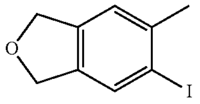

To a mixture of 5-methyl-1,3-dihydroisobenzofuran (1.00 g, 7.45 mmol), methanol (5.00 mL) and ethanol (5.00 mL), silver sulfate (4.65 g, 14.9 mmol) and iodine (1.89 g, 14.9 mmol) were gradually added at 0° C., and the mixture was stirred at the same temperature as above for 1 hour. Ice-cold water was added to the reaction mixture, followed by extraction with ethyl acetate. The organic layer was washed with saturated saline and dried over sodium sulfate, and the solvent was distilled off under reduced pressure. The residue was purified by silica gel column chromatography (hexane/ethyl acetate) to obtain the title compound (0.60 g).

1H NMR (400 MHZ, $CDCl_3$) δ 7.68 (s, 1H), 7.11 (s, 1H), 5.03 (d, 4H, J=5.2 Hz), 2.44 (s, 3H).

Production Example 3-4

N-(4,5-dimethylisoxazol-3-yl)-N-(methoxymethyl)-2-((6-methyl-1,3-dihydroisobenzofuran-5-yl)ethynyl)pyridine-3-sulfonamide

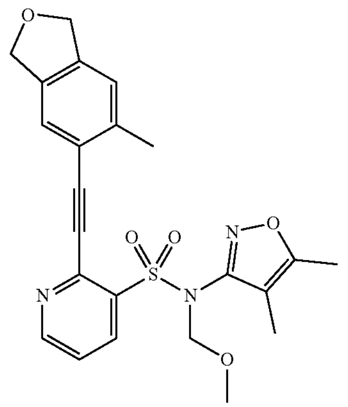 [SMILES: COCN(c1noc(C)c1C)S(=O)(=O)c1cccnc1C#Cc1cc2c(cc1C)COC2]

In an argon atmosphere, to a mixture of N-(4,5-dimethylisoxazol-3-yl)-2-ethynyl-N-(methoxymethyl)pyridine-3-sulfonamide (2.50 g, 7.78 mmol), 5-iodo-6-methyl-1,3-dihydroisobenzofuran (2.23 g, 8.56 mmol), triethylamine (2.19 mL, 15.6 mmol) and toluene (30.0 mL), bis(triphenylphosphine)palladium(II) dichloride (899 mg, 0.778 mmol) and copper(I) iodide (148 mg, 0.778 mmol) were added, and the reaction mixture was stirred at 65° C. for 6 hours. Ice-cold water was added to the reaction mixture, followed by extraction with ethyl acetate. The organic layer was washed with saturated saline and dried over sodium sulfate, and the solvent was distilled off under reduced pressure. The residue was purified by silica gel column chromatography (hexane/ethyl acetate) to obtain the title compound (1.60 g).

ESI-MS: m/z 454.27 [M+1]+

Example 3

N-(4,5-Dimethylisoxazol-3-yl)-2-((6-methyl-1,3-dihydroisobenzofuran-5-yl)ethynyl)pyridine-3-sulfonamide

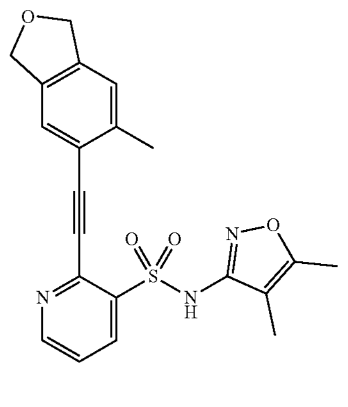 [SMILES: Cc1cc2c(cc1C#Cc1ncccc1S(=O)(=O)Nc1noc(C)c1C)COC2]

To a mixture of N-(4,5-dimethylisoxazol-3-yl)-N-(methoxymethyl)-2-((6-methyl-1,3-dihydroisobenzofuran-5-yl)ethynyl)pyridine-3-sulfonamide (1.00 g, 2.21 mmol) and methanol (10.0 mL), 6 mol/L hydrochloric acid (5.0 mL) was added at room temperature, and the reaction mixture was stirred at 60° C. for 16 hours. The reaction mixture was brought back to room temperature, and the solvent was distilled off under reduced pressure. Ethyl acetate was added to the residue. The organic layer was washed with water and dried over sodium sulfate, and the solvent was distilled off under reduced pressure. The residue was purified by silica gel column chromatography (hexane/ethyl acetate) to obtain the title compound (0.110 g).

1H NMR (400 MHZ, DMSO-$d_6$) δ 11.03 (s, 1H), 8.82 (dd, 1H, J=4.8, 1.6 Hz), 8.33 (dd, 1H, J=8.4, 1.6 Hz), 7.63-7.60 (m, 1H), 7.50 (bs, 1H), 7.29 (bs, 1H), 5.00 (s, 4H), 2.50 (s, 3H), 2.10 (s, 3H), 1.80 (s, 3H).

Production Example 4-1

N-(4,5-Dimethylisoxazol-3-yl)-N-(methoxymethyl)-2-((6-methyl-3-oxo-1,3-dihydroisobenzofuran-5-yl)ethynyl)pyridine-3-sulfonamide

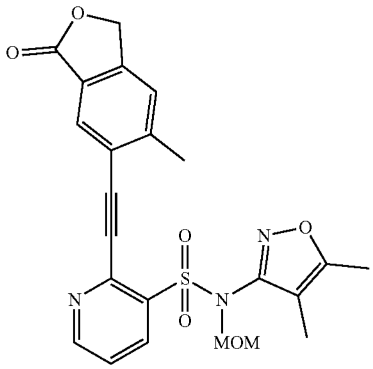

In an argon atmosphere, to a mixture of N-(4,5-dimethylisoxazol-3-yl)-2-ethynyl-N-(methoxymethyl)pyridine-3-sulfonamide (0.4 g, 1.24 mmol) and N, N-dimethylformamide (5 mL), 6-bromo-5-methylisobenzofuran-1 (3H)-one (0.366 g, 1.61 mmol), copper(I) iodide (47 mg, 0.24 mmol), triethylamine (0.35 mL, 2.48 mmol), and tetrakis(triphenylphosphine)palladium(0) (143 mg, 0.12 mmol) were added, and the reaction mixture was stirred at 80° C. for 4 hours. The reaction mixture was brought back to room temperature, and ice-cold water was added thereto, followed by extraction with ethyl acetate. The organic layer was washed with saturated saline and dried over sodium sulfate, and the solvent was distilled off under reduced pressure. The residue was purified by high-performance liquid chromatography (Luna C8 (250×50 mm) 10 μm, 0.1% aqueous formic acid solution/acetonitrile) to obtain the title compound (50 mg).

ESI-MS: m/z 468.24 [M+1]+

Example 4

N-(4,5-Dimethylisoxazol-3-yl)-2-((6-methyl-3-oxo-1,3-dihydroisobenzofuran-5-yl)ethynyl)pyridine-3-sulfonamide

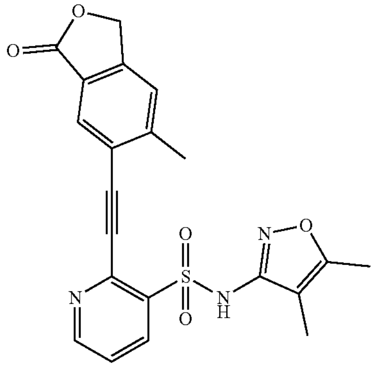 [SMILES: Cc1cc2c(cc1C#Cc1ncccc1S(=O)(=O)Nc1noc(C)c1C)C(=O)OC2]

To a mixture of N-(4,5-dimethylisoxazol-3-yl)-N-(methoxymethyl)-2-((6-methyl-3-oxo-1,3-dihydroisobenzofuran-5-yl)ethynyl)pyridine-3-sulfonamide (50 mg, 0.10 mmol) and methanol (5 mL), 6 mol/L hydrochloric acid (1 mL) was added at 0° C., and the reaction mixture was stirred at 50° C. for 4 hours. The reaction mixture was brought back to room temperature, and ice-cold water was added thereto, followed by extraction with ethyl acetate. The organic layer was washed with saturated saline and dried over sodium sulfate, and the solvent was distilled off under reduced pressure. The residue was purified by high-performance liquid chromatography (Luna C18 (250×50 mm) 10 μm, 0.1% aqueous formic acid solution/acetonitrile) to obtain the title compound (12 mg).

ESI-MS: m/z 424.18 [M+1]+

1H NMR (400 MHZ, DMSO-$d_6$) δ11.21 (s, 1H), 8.86 (t, J=5.2 Hz, 1H), 8.37 (t, J=5.2 Hz, 1H), 8.08 (d, J=4.8 Hz, 1H), 7.67 (t, J=4.8 Hz, 2H), 5.45 (d, J=5.2 Hz, 2H), 2.61 (d, J=5.2 Hz, 3H), 2.11 (d, J=5.2 Hz, 3H), 1.81 (d, J=5.2 Hz, 3H).

Production Example 5-1

2-((1,3-Dihydroisobenzofuran-5-yl)ethynyl)-N-(4,5-dimethylisoxazol-3-yl)-N-(methoxymethyl)pyridine-3-sulfonamide

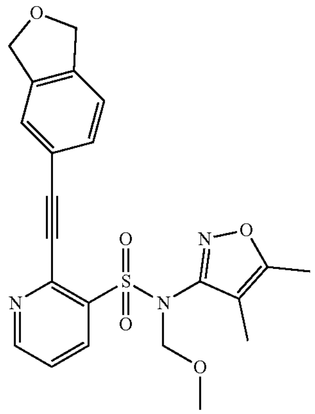 [SMILES: COCN(c1noc(C)c1C)S(=O)(=O)c1cccnc1C#Cc1ccc2c(c1)COC2]

In an argon atmosphere, to a mixture of N-(4,5-dimethylisoxazol-3-yl)-2-ethynyl-N-(methoxymethyl)pyridine-3-sulfonamide (250 mg, 0.778 mmol) and toluene (10 mL), 5-bromo-1,3-dihydroisobenzofuran (170 mg, 0.856 mmol), copper(I) iodide (15 mg, 0.077 mmol), triethylamine (0.22 mL, 1.56 mmol), and tetrakis(triphenylphosphine)palladium (0) (90 mg, 0.077 mmol) were added, and the reaction mixture was stirred at 80° C. for 4 hours. The reaction mixture was brought back to room temperature, and ice-cold water was added thereto, followed by extraction with ethyl acetate. The organic layer was washed with saturated saline and dried over sodium sulfate, and the solvent was distilled off under reduced pressure. The residue was purified by high-performance liquid chromatography (Luna C18 (250×50 mm) 10 μm, 0.1% aqueous formic acid solution/acetonitrile) to obtain the title compound (50 mg).

ESI-MS: m/z 440.27 [M+1]+

Example 5

2-((1,3-Dihydroisobenzofuran-5-yl)ethynyl)-N-(4,5-dimethylisoxazol-3-yl)pyridine-3-sulfonamide

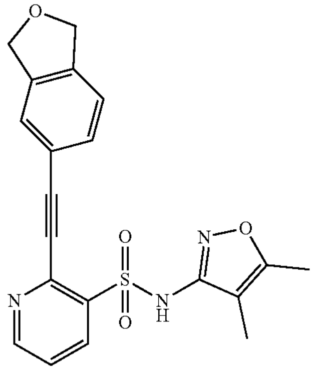 [SMILES: Cc1onc(NS(=O)(=O)c2cccnc2C#Cc2ccc3c(c2)COC3)c1C]

To a mixture of 2-((1,3-dihydroisobenzofuran-5-yl)ethynyl)-N-(4,5-dimethylisoxazol-3-yl)-N-(methoxymethyl) pyridine-3-sulfonamide (100 mg, 0.227 mmol) and methanol (5 mL), 6 mol/L hydrochloric acid (1 mL) was added at 0° C., and the reaction mixture was stirred at 50° C. for 8 hours. The reaction mixture was brought back to room temperature, and ice-cold water was added thereto, followed by extraction with ethyl acetate. The organic layer was washed with a saturated aqueous solution of sodium bicarbonate and saturated saline and dried over sodium sulfate, and the solvent was distilled off under reduced pressure. The residue was purified by high-performance liquid chromatography (Luna C18 (250×50 mm) 10 μm, 0.1% aqueous formic acid solution/acetonitrile) to obtain the title compound (16 mg).

ESI-MS: m/z 396.23 [M+1]+

1H NMR (400 MHZ, DMSO-d6): δ11.10 (s, 1H), 8.80 (s, 1H), 8.34 (t, J=6.4 Hz, 1H), 7.63 (t, J=13.2 Hz, 1H), 7.57-7.53 (m, 2H), 7.44 (t, J=6.4 Hz, 1H), 5.05 (d, J=8 Hz, 1H), 3.33 (s, 3H), 2.09 (s, 3H), 1.80 (s, 3H).

Production Example 6-1

5-Chloro-6-iodoisobenzofuran-1 (3H)-one

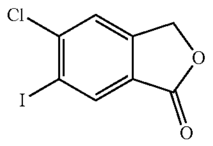 [SMILES: O=C1OCc2cc(Cl)c(I)cc21]

In an argon atmosphere, to a mixture of 4-chloro-3-iodobenzoic acid (1.0 g, 3.5 mmol), 1,1-dibromomethane (15 mL), and dipotassium hydrogen phosphate (2.25 g, 10.6 mmol), palladium(II)acetate (80 mg, 0.35 mmol) was added, and the reaction mixture was stirred at 140° C. for 16 hours. The reaction mixture was brought back to room temperature, and filtered through celite while washed with ethyl acetate. The filtrate was washed with water and saturated saline and dried over sodium sulfate, and the solvent was distilled off under reduced pressure. The residue was purified by silica gel column chromatography (hexane/ethyl acetate) to obtain the title compound (0.4 g).

1H NMR (400 MHZ, DMSO-d6): δ 8.35 (s, 1H), 7.97 (s, 1H), 5.34 (s, 2H).

Production Example 6-2

5-Chloro-6-iodo-1,3-dihydroisobenzofuran-1-ol

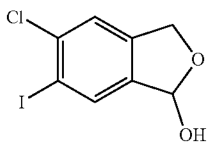 [SMILES: OC1OCc2cc(Cl)c(I)cc21]

To a mixture of 5-chloro-6-iodoisobenzofuran-1 (3H)-one (200 mg, 0.680 mmol) and dichloromethane (30 mL), diisobutyl aluminum hydride (20% solution in toluene, 1.7 mL, 2.0 mmol) was added at −78° C., and the mixture was stirred at the same temperature as above for 2 hours. A saturated aqueous solution of ammonium chloride was added to the reaction mixture, and filtered through celite while washed with ethyl acetate. The filtrate was washed with water and saturated saline and dried over sodium sulfate, and the solvent was distilled off under reduced pressure. The residue was purified by silica gel column chromatography (hexane/ethyl acetate) to obtain the title compound (70 mg).

1H NMR (400 MHZ, DMSO-d6): δ 7.89 (s, 1H), 7.61 (s, 1H), 6.89 (d, J=7.6 Hz, 1H), 6.75 (dd, J=7.6, 8.0 Hz, 1H), 4.99 (d, J=13.6 Hz, 1H), 4.84 (d, J=12.8 Hz, 1H), 4.83 (d, J=13.6 Hz, 1H).

Production Example 6-3

5-Chloro-6-iodo-1,3-dihydroisobenzofuran

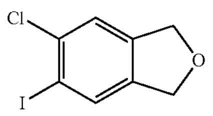

To a mixture of 5-chloro-6-iodo-1,3-dihydroisobenzofuran-1-ol (300 mg, 1.01 mmol) and dichloromethane (26 mL), trifluoroacetic acid (0.11 mL, 1.5 mmol) and triethylsilane (0.4 mL, 2.6 mmol) were added at room temperature, and the mixture was stirred at the same temperature as above for 4 hours. A saturated aqueous solution of sodium bicarbonate was added to the reaction mixture, followed by extraction with dichloromethane. The organic layer was washed with saturated saline and dried over sodium sulfate, and the solvent was distilled off under reduced pressure. The residue was purified by silica gel column chromatography (hexane/ethyl acetate) to obtain the title compound (200 mg).

1H NMR (400 MHZ, DMSO-d6): δ 7.90 (s, 1H), 7.56 (s, 1H), 4.94 (s, 4H).

Production Example 6-4

2-((6-Chloro-1,3-dihydroisobenzofuran-5-yl)ethynyl)-N-(4,5-dimethylisoxazol-3-yl)-N-(methoxymethyl)pyridine-3-sulfonamide

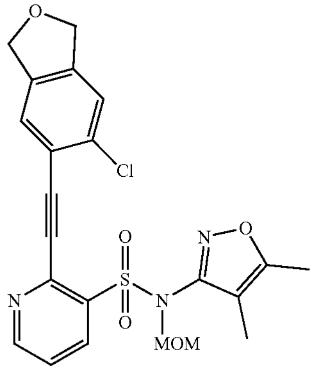

In an argon atmosphere, to a mixture of N-(4,5-dimethylisoxazol-3-yl)-2-ethynyl-N-(methoxymethyl)pyridine-3-sulfonamide (120 mg, 0.373 mmol) and N, N-dimethylformamide (5 mL), 5-chloro-6-iodo-1,3-dihydroisobenzofuran (126 mg, 0.448 mmol), copper(I) iodide (7.08 mg, 0.037 mmol), triethylamine (0.16 mL, 1.12 mmol), and tetrakis (triphenylphosphine)palladium(0) (43 mg, 0.037 mmol) were added, and the reaction mixture was stirred at 60° C. for 2 hours. The reaction mixture was brought back to room temperature, and ice-cold water was added thereto, followed by extraction with ethyl acetate. The organic layer was washed with saturated saline and dried over sodium sulfate, and the solvent was distilled off under reduced pressure. The residue was purified by silica gel column chromatography (hexane/ethyl acetate) to obtain the title compound (95 mg).

ESI-MS: m/z 473.9 [M+1]+

Example 6

2-((6-Chloro-1,3-dihydroisobenzofuran-5-yl)ethynyl)-N-(4,5-dimethylisoxazol-3-yl)pyridine-3-sulfonamide

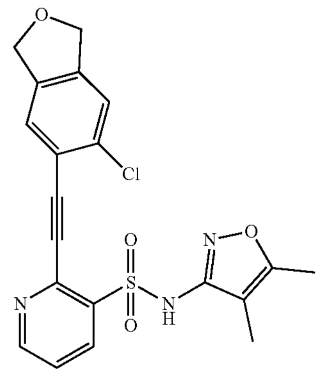 [SMILES: Cc1onc(NS(=O)(=O)c2cccnc2C#Cc2cc3c(cc2Cl)COC3)c1C]

To a mixture of 2-((6-chloro-1,3-dihydroisobenzofuran-5-yl)ethynyl)-N-(4,5-dimethylisoxazol-3-yl)-N-(methoxymethyl)pyridine-3-sulfonamide (120 mg, 0.253 mmol), methanol (5 mL), and acetonitrile (1 mL), 50% sulfuric acid (1.2 mL) was added at 0° C., and the reaction mixture was stirred at 60° C. for 2 hours. The reaction mixture was brought back to room temperature, a saturated aqueous solution of sodium bicarbonate was added thereto, followed by extraction with ethyl acetate. The organic layer was washed with saturated saline and dried over sodium sulfate, and the solvent was distilled off under reduced pressure. The residue was purified by high-performance liquid chromatography (Kinetex penta C18 (250×50 mm) 5 μm, 0.1% aqueous trifluoroacetic acid solution/acetonitrile) to obtain the title compound (40 mg).

ESI-MS: m/z 430.01 [M+1]+

1H NMR (400 MHZ, DMSO-d6): δ 11.08 (s, 1H), 8.84 (d, J=4.0 Hz, 1H), 8.34 (d, J=8.4 Hz, 1H), 7.69-7.65 (m, 1H), 7.64 (s, 1H), 7.61 (s, 1H), 4.14 (s, 4H), 2.11 (s, 3H), 1.79 (s, 3H).

Production Example 7-1

2-(2-(Hydroxymethyl)-4-methylphenyl) propan-2-ol

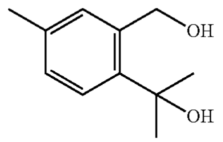

To a mixture of 5-methylisobenzofuran-1 (3H)-one (2.40 g, 16.2 mmol) and tetrahydrofuran (30 mL), methyl magnesium bromide (3.0 M solution in ether, 16.2 mL, 48.6 mmol) was added at 0° C., and the mixture was stirred at room temperature for 3 hours. A saturated aqueous solution of ammonium chloride was added to the reaction mixture, followed by extraction with ethyl acetate. The organic layer was washed with saturated saline and dried over sodium sulfate, and the solvent was distilled off under reduced pressure. The residue was purified by silica gel column chromatography (hexane/ethyl acetate) to obtain the title compound (1.30 g).

1H NMR (400 Hz, DMSO-d6) δ 7.30 (s, 1H), 7.19 (d, J=8.0 Hz, 1H), 6.95 (d, J=8.0 Hz, 1H), 5.09 (s, 1H), 4.98 (t, J=5.6 Hz, 1H), 4.75 (d, J=5.6 Hz, 2H), 2.25 (s, 3H), 1.46 (s, 6H).

Production Example 7-2

1,1,5-Trimethyl-1,3-dihydroisobenzofuran

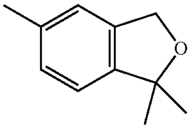

To a mixture of 2-(2-(hydroxymethyl)-4-methylphenyl) propan-2-ol (1.30 g, 7.22 mmol) and tetrahydrofuran (20 mL), 50% sodium hydride (0.69 g, 14.4 mmol) was gradually added at 0° C., and the mixture was stirred at room temperature for 1 hour. Trimethyl phosphate (2.01 g, 14.4 mmol) was gradually added to the reaction mixture at room temperature, and the mixture was stirred at the same temperature as above for 4 hours. Ice-cold water was added to the reaction mixture, followed by extraction with ethyl acetate. The organic layer was washed with saturated saline and dried over sodium sulfate, and the solvent was distilled off under reduced pressure. The residue was purified by silica gel column chromatography (hexane/ethyl acetate) to obtain the title compound (0.60 g).

1H NMR (400 Hz, DMSO-d6) δ 7.11 (d, J=7.6 Hz, 1H), 7.04 (t, J=4.8 Hz, 2H), 4.89 (s, 2H), 2.29 (s, 3H), 1.37 (s, 6H).

Production Example 7-3

6-Iodo-1,1,5-trimethyl-1,3-dihydroisobenzofuran

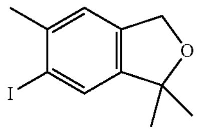

To a mixture of 1,1,5-trimethyl-1,3-dihydroisobenzofuran (0.60 g, 3.7 mmol) and dichloromethane (10 mL), N-iodosuccinimide (1.60 g, 7.40 mmol) and trifluoromethanesulfonic acid (1.10 g, 7.40 mmol) were gradually added at 0° C., and the mixture was stirred at the same temperature as above for 2 hours. A 10% aqueous sodium thiosulfate solution was added to the reaction mixture, followed by extraction with dichloromethane. The organic layer was washed with saturated saline and dried over sodium sulfate, and the solvent was distilled off under reduced pressure. The residue was purified by silica gel column chromatography (hexane/ethyl acetate) to obtain the title compound (0.30 g).

1H NMR (400 Hz, DMSO-d6) δ 7.71 (s, 1H), 7.22 (s, 1H), 4.86 (s, 2H), 2.35 (s, 3H), 1.38 (s, 6H).

Production Example 7-4

2-Chloro-N-(4-chloro-5-methylisoxazol-3-yl)pyridine-3-sulfonamide

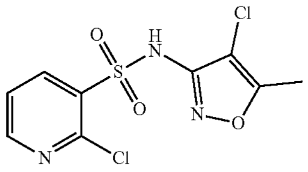 [SMILES: Cc1onc(NS(=O)(=O)c2cccnc2Cl)c1Cl]

To a mixture of 4-chloro-5-methylisoxazol-3-amine (2.98 g, 22.6 mmol) and pyridine (50 mL), 4-dimethylaminopyridine (0.69 g, 5.66 mmol) and 2-chloropyridine-3-sulfonyl chloride (4.0 g, 18.8 mmol) were gradually added at 0° C., and the reaction mixture was stirred at 55° C. for 16 hours. Ice-cold water was added to the reaction mixture, followed by extraction with ethyl acetate. The organic layer was washed with 2 N hydrochloric acid and saturated saline and dried over sodium sulfate. The solvent was distilled off under reduced pressure to obtain the title compound (1.90 g) in a crude form. This compound was used in the next reaction without being further purified.

ESI-MS: m/z 307.98 [M+1]+

Production Example 7-5

2-Chloro-N-(4-chloro-5-methylisoxazol-3-yl)-N-(methoxymethyl)pyridine-3-sulfonamide

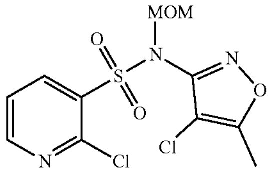

To a mixture of 2-chloro-N-(4-chloro-5-methylisoxazol-3-yl)pyridine-3-sulfonamide (1.90 g, 6.98 mmol) and N, N-dimethylformamide (20.0 mL), 50% sodium hydride (594 mg, 12.3 mmol) was gradually added at 0° C., and the mixture was stirred at the same temperature as above for 30 minutes. Chloromethyl methyl ether (0.69 mL, 9.28 mmol) was gradually added to the reaction mixture, and the mixture was stirred at room temperature for 3 hours. Ice-cold water was added to the reaction mixture, followed by extraction with ethyl acetate. The organic layer was washed with saturated saline and dried over sodium sulfate, and the solvent was distilled off under reduced pressure. The residue was purified by silica gel column chromatography (hexane/ethyl acetate) to obtain the title compound (1.0 g).

1H NMR (400 Hz, DMSO-d6) δ 8.71 (d, J=4.4 Hz, 1H), 8.39 (d, J=8.0 Hz, 1H), 7.66 (dd, J=7.6 Hz, 4.8 Hz, 1H), 5.20 (s, 2H), 3.39 (s, 3H), 2.43 (s, 3H).

Production Example 7-6

N-(4-Chloro-5-methylisoxazol-3-yl)-N-(methoxymethyl)-2-((triisopropylsilyl)ethynyl)pyridine-3-sulfonamide

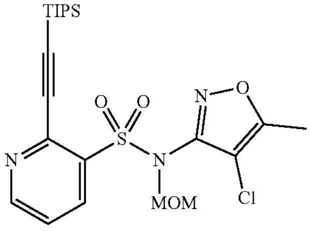

In an argon atmosphere, to a mixture of 2-chloro-N-(4-chloro-5-methylisoxazol-3-yl)-N-(methoxymethyl)pyridine-3-sulfonamide (1.20 g, 3.41 mmol), triethylamine (1.44 mL, 10.2 mmol), triisopropylsilylacetylene (1.24 g, 6.83 mmol), and tetrahydrofuran (15 mL), bis(triphenylphosphine)palladium(II) dichloride (239 mg, 0.34 mmol) and copper(I) iodide (20 mg, 0.10 mmol) were added, and the reaction mixture was stirred at 55° C. for 6 hours. The reaction mixture was brought back to room temperature, and ice-cold water was added thereto, followed by extraction with ethyl acetate. The organic layer was washed with saturated saline and dried over sodium sulfate, and the solvent was distilled off under reduced pressure. The residue was purified by silica gel column chromatography (hexane/ethyl acetate) to obtain the title compound (0.70 g).

1H NMR (400 Hz, DMSO-d6) δ 8.83 (d, J=3.6 Hz, 1H), 8.28 (t, J=7.2 Hz, 1H), 7.62-7.66 (m, 1H), 5.19 (s, 2H), 3.33 (d, J=6.0 Hz, 3H), 2.43 (s, 3H), 1.10 (d, J=3.6 Hz, 21H).

Production Example 7-7

N-(4-Chloro-5-methylisoxazol-3-yl)-2-ethynyl-N-(methoxymethyl)pyridine-3-sulfonamide

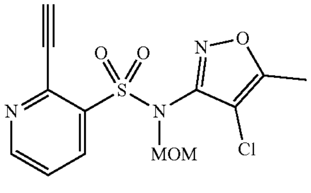

To a mixture of N-(4-chloro-5-methylisoxazol-3-yl)-N-(methoxymethyl)-2-((triisopropylsilyl)ethynyl)pyridine-3-sulfonamide (0.70 g, 1.4 mmol) and tetrahydrofuran (10 mL), tetrabutylammonium fluoride (1 mol/L solution in tetrahydrofuran, 2.81 mL, 2.81 mmol) was gradually added at 0° C., and the reaction mixture was stirred at room temperature for 2 hours. Ice-cold water was added to the reaction mixture, followed by extraction with ethyl acetate. The organic layer was washed with saturated saline and dried over sodium sulfate, and the solvent was distilled off under reduced pressure. The residue was purified by silica gel column chromatography (hexane/ethyl acetate) to obtain the title compound (0.38 g).

ESI-MS: m/z 342.15 [M+1]+

Production Example 7-8

N-(4-Chloro-5-methylisoxazol-3-yl)-N-(methoxymethyl)-2-((3,3,6-trimethyl-1,3-dihydroisobenzofuran-5-yl)ethynyl)pyridine-3-sulfonamide

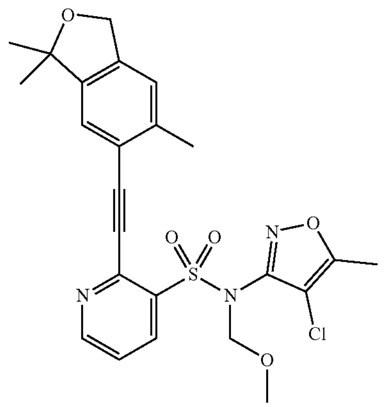

In an argon atmosphere, to a mixture of N-(4-chloro-5-methylisoxazol-3-yl)-2-ethynyl-N-(methoxymethyl)pyridine-3-sulfonamide (0.38 g, 1.11 mmol) and toluene (5 mL), 6-iodo-1,1,5-trimethyl-1,3-dihydroisobenzofuran (0.32 g, 1.11 mmol), copper(I) iodide (6.35 mg, 0.03 mmol), triethylamine (0.46 mL, 3.34 mmol), and tetrakis(triphenylphosphine)palladium(0) (128 mg, 0.11 mmol) were added, and the reaction mixture was stirred at 65° C. for 6 hours. The reaction mixture was brought back to room temperature, and water was added thereto, followed by extraction with ethyl acetate. The organic layer was washed with saturated saline and dried over sodium sulfate, and the solvent was distilled off under reduced pressure. The residue was purified by silica gel column chromatography (hexane/ethyl acetate) to obtain the title compound (0.25 g).

ESI-MS: m/z 502.10 [M+1]+

Example 7

N-(4-Chloro-5-methylisoxazol-3-yl)-2-((3,3,6-trimethyl-1,3-dihydroisobenzofuran-5-yl)ethynyl)pyridine-3-sulfonamide

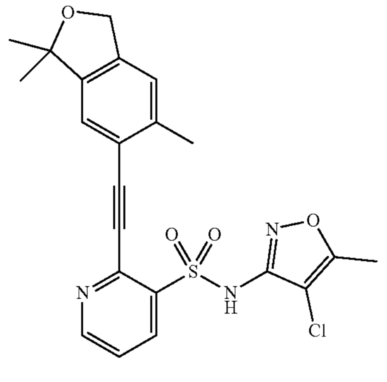

To a mixture of N-(4-chloro-5-methylisoxazol-3-yl)-N-(methoxymethyl)-2-((3,3,6-trimethyl-1,3-dihydroisobenzofuran-5-yl)ethynyl)pyridine-3-sulfonamide (0.25 g, 0.49 mmol) and methanol (3 mL), 6 mol/L hydrochloric acid (3 mL) was added at 0° C., and the reaction mixture was stirred at 60° C. for 16 hours. The solvent in the reaction mixture was distilled off under reduced pressure, and a saturated aqueous solution of sodium bicarbonate was added to the residue, followed by extraction with ethyl acetate. The organic layer was washed with saturated saline and dried over sodium sulfate, and the solvent was distilled off under reduced pressure. The residue was purified by silica gel column chromatography (hexane/ethyl acetate) to obtain the title compound (35 mg).

ESI-MS: m/z 458.08 [M+1]+

1H-NMR (400 Hz, DMSO-d6) δ 8.52 (d, J=3.6 Hz, 1H), 8.19 (d, J=8.0, 1H), 7.46 (s, 1H), 7.39 (dd, J=8.0, 4.8 Hz, 1H), 7.18 (s, 1H), 4.94 (s, 2H), 2.54 (s, 3H), 2.11 (s, 3H), 1.42 (s, 6H).

Production Example 8-1

2-Chloro-N-(3,4-dimethylisoxazol-5-yl)pyridine-3-sulfonamide

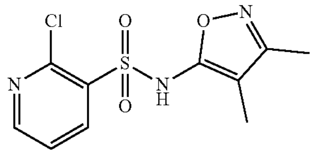 [SMILES: Cc1noc(NS(=O)(=O)c2cccnc2Cl)c1C]

To a mixture of 3,4-dimethylisoxazol-5-amine (1.0 g, 8.9 mmol) and pyridine (10 mL), 4-dimethylaminopyridine (108 mg, 0.89 mmol) and 2-chloropyridine-3-sulfonyl chloride (2.8 g, 13.2 mmol) were gradually added at room temperature, and the reaction mixture was stirred at 50° C. for 16 hours. Ice-cold water was added to the reaction mixture, followed by extraction with ethyl acetate. The organic layer was washed with 2 N hydrochloric acid and dried over sodium sulfate, and the solvent was distilled off under reduced pressure. The residue was purified by silica gel column chromatography (hexane/ethyl acetate) to obtain the title compound (2.0 g).

ESI-MS: m/z 287.9 [M+1]+

Production Example 8-2

2-Chloro-N-(3,4-dimethylisoxazol-5-yl)-N-(methoxymethyl)pyridine-3-sulfonamide

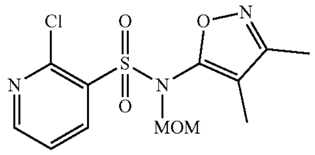

To a mixture of 2-chloro-N-(3,4-dimethylisoxazol-5-yl)pyridine-3-sulfonamide (2.0 g, 7.0 mmol) and N, N-dimethylformamide (10 mL), 60% sodium hydride (334 mg, 13.9 mmol) was gradually added at 0° C., and the mixture was stirred at the same temperature as above for 30 minutes. Chloromethyl methyl ether (0.83 g, 10.5 mmol) was gradually added to the reaction mixture, and the mixture was stirred at room temperature for 2 hours. Ice-cold water was added to the reaction mixture, followed by extraction with ethyl acetate. The organic layer was washed with saturated saline and dried over sodium sulfate, and the solvent was distilled off under reduced pressure. The residue was purified by silica gel column chromatography (hexane/ethyl acetate) to obtain the title compound (2.0 g).

ESI-MS: m/z 332.18 [M+1]+

Production Example 8-3

N-(3,4-Dimethylisoxazol-5-yl)-N-(methoxymethyl)-2-((triisopropylsilyl)ethynyl)pyridine-3-sulfonamide

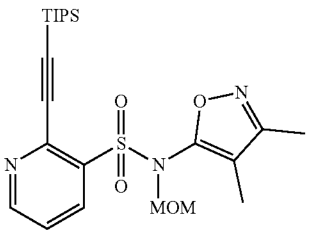

In an argon atmosphere, to a mixture of 2-chloro-N-(3,4-dimethylisoxazol-5-yl)-N-(methoxymethyl)pyridine-3-sulfonamide (2.0 g, 6.0 mmol), triethylamine (1.8 g, 18 mmol), triisopropylsilylacetylene (1.65 g, 9.06 mmol), and N, N-dimethylformamide (10 mL), bis(triphenylphosphine) palladium(II) dichloride (150 mg, 0.604 mmol) and copper (I) iodide (114 mg, 0.604 mmol) were added, and the reaction mixture was stirred at 100° C. for 16 hours. The reaction mixture was brought back to room temperature, and ice-cold water was added thereto, followed by extraction with ethyl acetate. The organic layer was washed with saturated saline and dried over sodium sulfate, and the solvent was distilled off under reduced pressure. The residue was purified by silica gel column chromatography (hexane/ethyl acetate) to obtain the title compound (1.5 g).

ESI-MS: m/z 478.1 [M+1]+

Production Example 8-4

N-(3,4-Dimethylisoxazol-5-yl)-2-ethynyl-N-(methoxymethyl)pyridine-3-sulfonamide

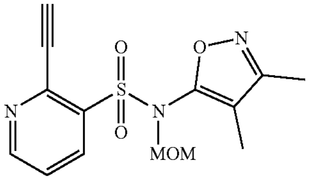

To a mixture of N-(3,4-dimethylisoxazol-5-yl)-N-(methoxymethyl)-2-((triisopropylsilyl)ethynyl)pyridine-3-sulfonamide (1.0 g, 2.1 mmol) and tetrahydrofuran (10 mL), tetrabutylammonium fluoride (1 mol/L solution in tetrahydrofuran, 3.1 mL, 3.1 mmol) was gradually added at 0° C., and the reaction mixture was stirred at room temperature for 1 hour. Water was added to the reaction mixture, followed by extraction with ethyl acetate. The organic layer was dried over sodium sulfate, and the solvent was distilled off under reduced pressure. The residue was purified by silica gel column chromatography (hexane/ethyl acetate) to obtain the title compound (350 mg).

ESI-MS: m/z 322.0 [M+1]+

Production Example 8-5

N-(3,4-Dimethylisoxazol-5-yl)-N-(methoxymethyl)-2-((3,3,6-trimethyl-1,3-dihydroisobenzofuran-5-yl)ethynyl)pyridine-3-sulfonamide

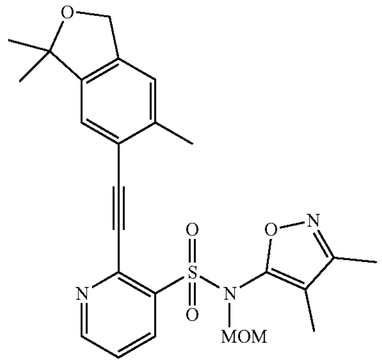

In an argon atmosphere, to a mixture of N-(3,4-dimethylisoxazol-5-yl)-2-ethynyl-N-(methoxymethyl)pyridine-3-sulfonamide (300 mg, 0.93 mmol) and N, N-dimethylformamide (3 mL), 6-iodo-1,1,5-trimethyl-1,3-dihydroisobenzofuran (296 mg, 1.02 mmol), copper(I) iodide (17 mg, 0.09 mmol), triethylamine (282 mg, 2.79 mmol), and tetrakis(triphenylphosphine)palladium(0) (103 mg, 0.09 mmol) were added, and the reaction mixture was stirred at room temperature for 1 hour. Ice-cold water was added to the reaction mixture, followed by extraction with ethyl acetate. The organic layer was washed with saturated saline and dried over sodium sulfate, and the solvent was distilled off under reduced pressure. The residue was purified by silica gel column chromatography (hexane/ethyl acetate) to obtain the title compound (250 mg).

ESI-MS: m/z 482.39 [M+1]+

Example 8

N-(3,4-Dimethylisoxazol-5-yl)-2-((3,3,6-trimethyl-1,3-dihydroisobenzofuran-5-yl)ethynyl)pyridine-3-sulfonamide

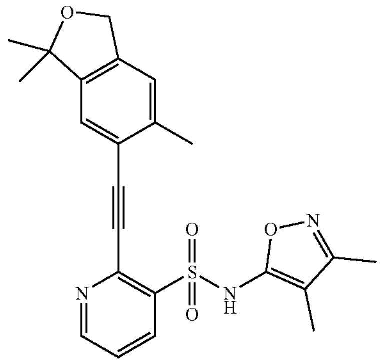

To a mixture of N-(3,4-dimethylisoxazol-5-yl)-N-(methoxymethyl)-2-((3,3,6-trimethyl-1,3-dihydroisobenzofuran-5-yl)ethynyl)pyridine-3-sulfonamide (200 mg, 0.415 mmol) and methanol (4 mL), 50% sulfuric acid (4 mL) was added at 0° C., and the reaction mixture was stirred at 50° C. for 1 hour. The solvent in the reaction mixture was distilled off under reduced pressure, and a saturated aqueous solution of sodium bicarbonate was added to the residue, followed by extraction with ethyl acetate. The organic layer was washed with saturated saline and dried over sodium sulfate, and the solvent was distilled off under reduced pressure. The residue was purified by high-performance liquid chromatography (Luna C18 (250×50 mm) 10 μm, 0.1% aqueous formic acid solution/acetonitrile) to obtain the title compound (60 mg).

ESI-MS: m/z 438.31 [M+1]+

1H NMR (400 MHZ, DMSO-d6): δ 11.25 (s, 1H), 8.79 (s, 1H), 8.30 (d, J=7.2 Hz, 1H), 7.609 (s, 1H), 7.390 (s, 1H), 7.224 (s, 1H), 4.95 (s, 2H), 2.46 (s, 3H), 1.82 (s, 3H), 1.66 (s, 3H), 1.43 (s, 6H).

Production Example 9-1

2-Chloro-N-(4-chloro-3-methylisoxazol-5-yl)pyridine-3-sulfonamide

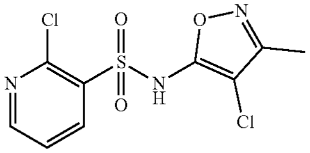 [SMILES: Cc1noc(NS(=O)(=O)c2cccnc2Cl)c1Cl]

To a mixture of 4-chloro-3-methylisoxazol-5-amine (1.5 g, 11.4 mmol) and tetrahydrofuran (15 mL), 60% sodium hydride (909 mg, 22.7 mmol) and 2-chloropyridine-3-sulfonyl chloride (2.89 g, 13.6 mmol) were gradually added at 0° C., and the mixture was stirred at room temperature for 1 hour. Ice-cold water was added to the reaction mixture, followed by extraction with ethyl acetate. The organic layer was washed with saturated saline and dried over sodium sulfate, and the solvent was distilled off under reduced pressure. The residue was purified by silica gel column chromatography (hexane/ethyl acetate) to obtain the title compound (2.5 g).

ESI-MS: m/z 307.9 [M+1]+

Production Example 9-2

2-Chloro-N-(4-chloro-3-methylisoxazol-5-yl)-N-(methoxymethyl)pyridine-3-sulfonamide

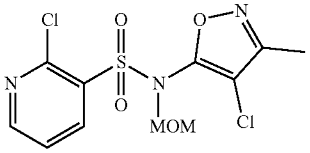

To a mixture of 2-chloro-N-(4-chloro-3-methylisoxazol-5-yl)pyridine-3-sulfonamide (1.8 g, 5.8 mmol) and N, N-dimethylformamide (20 mL), 60% sodium hydride (467 mg, 11.7 mmol) was gradually added at 0° C., and the mixture was stirred at the same temperature as above for 30 minutes. Chloromethyl methyl ether (0.54 mL, 8.8 mmol) was gradually added to the reaction mixture, and the mixture was stirred at room temperature for 2 hours. Ice-cold water was added to the reaction mixture, followed by extraction with ethyl acetate. The organic layer was washed with saturated saline and dried over sodium sulfate, and the solvent was distilled off under reduced pressure. The residue was purified by silica gel column chromatography (hexane/ethyl acetate) to obtain the title compound (1.3 g).

ESI-MS: m/z 352.27 [M+1]+

Production Example 9-3

N-(4-Chloro-3-methylisoxazol-5-yl)-N-(methoxymethyl)-2-((triisopropylsilyl)ethynyl)pyridine-3-sulfonamide

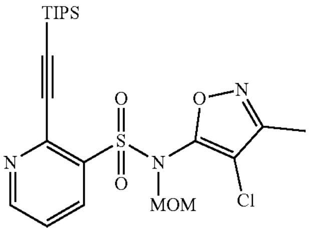

In an argon atmosphere, to a mixture of 2-chloro-N-(4-chloro-3-methylisoxazol-5-yl)-N-(methoxymethyl)pyridine-3-sulfonamide (1.3 g, 3.7 mmol), triethylamine (1.46 mL, 11.1 mmol), triisopropylsilylacetylene (0.8 g, 4.4 mmol), and N, N-dimethylformamide (6.5 mL), bis(triphenylphosphine)palladium(II) dichloride (134 mg, 0.184 mmol) and copper(I) iodide (140 mg, 0.738 mmol) were added, and the reaction mixture was stirred at 100° C. for 4 hours. The reaction mixture was brought back to room temperature, and filtered through celite while washed with ethyl acetate. The filtrate was washed with water and saturated saline and dried over sodium sulfate, and the solvent was distilled off under reduced pressure. The residue was purified by silica gel column chromatography (hexane/ethyl acetate) to obtain the title compound (600 mg).

ESI-MS: m/z 498.51 [M+1]+

Production Example 9-4

N-(4-Chloro-3-methylisoxazol-5-yl)-2-ethynyl-N-(methoxymethyl)pyridine-3-sulfonamide

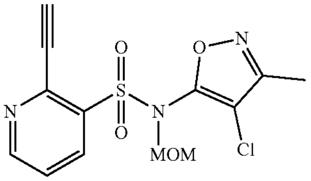

To a mixture of N-(4-chloro-3-methylisoxazol-5-yl)-N-(methoxymethyl)-2-((triisopropylsilyl)ethynyl)pyridine-3-sulfonamide (600 mg, 1.20 mmol) and tetrahydrofuran (10 mL), tetrabutylammonium fluoride (1 mol/L solution in tetrahydrofuran, 1.2 mL, 1.2 mmol) was gradually added at 0° C., and the reaction mixture was stirred at room temperature for 2 hours. Water was added to the reaction mixture, followed by extraction with ethyl acetate. The organic layer was dried over sodium sulfate, and the solvent was distilled off under reduced pressure. The residue was purified by silica gel column chromatography (hexane/ethyl acetate) to obtain the title compound (220 mg).

ESI-MS: m/z 342.0 [M+1]+

Production Example 9-5

N-(4-Chloro-3-methylisoxazol-5-yl)-N-(methoxymethyl)-2-((3,3,6-trimethyl-1,3-dihydroisobenzofuran-5-yl)ethynyl)pyridine-3-sulfonamide

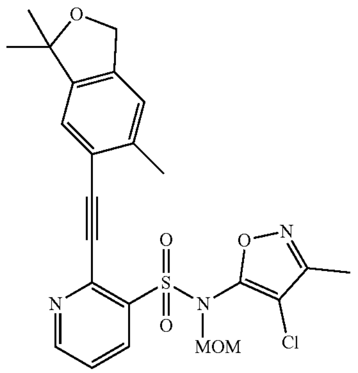

In an argon atmosphere, to a mixture of N-(4-chloro-3-methylisoxazol-5-yl)-2-ethynyl-N-(methoxymethyl)pyridine-3-sulfonamide (250 mg, 0.73 mmol) and N, N-dimethylformamide (5 mL), 6-iodo-1,1,5-trimethyl-1,3-dihydroisobenzofuran (232 mg, 0.81 mmol), copper(I) iodide (27 mg, 0.15 mmol), triethylamine (0.48 mL, 3.66 mmol), and tetrakis(triphenylphosphine)palladium(0) (84 mg, 0.073 mmol) were added, and the reaction mixture was stirred at room temperature for 30 minutes. Ice-cold water was added to the reaction mixture, followed by extraction with ethyl acetate. The organic layer was washed with saturated saline and dried over sodium sulfate, and the solvent was distilled off under reduced pressure. The residue was purified by silica gel column chromatography (hexane/ethyl acetate) to obtain the title compound (200 mg).

ESI-MS: m/z 502.56 [M+1]+

Example 9

N-(4-Chloro-3-methylisoxazol-5-yl)-2-((3,3,6-trimethyl-1,3-dihydroisobenzofuran-5-yl)ethynyl)pyridine-3-sulfonamide

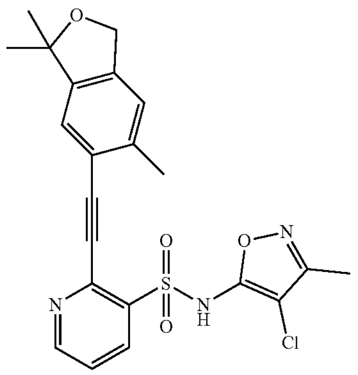

To a mixture of N-(4-chloro-3-methylisoxazol-5-yl)-N-(methoxymethyl)-2-((3,3,6-trimethyl-1,3-dihydroisobenzofuran-5-yl)ethynyl)pyridine-3-sulfonamide (200 mg, 0.39 mmol) and methanol (2 mL), 50% sulfuric acid (2 mL) was added at 0° C., and the reaction mixture was stirred at room temperature for 16 hours. The solvent in the reaction mixture was distilled off under reduced pressure, and a saturated aqueous solution of sodium bicarbonate was added to the residue, followed by extraction with ethyl acetate. The organic layer was washed with saturated saline and dried over sodium sulfate, and the solvent was distilled off under reduced pressure. The residue was recrystallized from diethyl ether to obtain the title compound (35 mg).

ESI-MS: m/z 458.36 [M+1]+

1H NMR (400 MHZ, DMSO-d6): δ 8.69 (d, J=3.6 Hz, 1H), 8.30 (dd, J=8.0 Hz, 1.2 Hz, 1H), 7.55-7.52 (m, 1H), 7.49 (s, 1H), 7.07 (s, 1H), 4.94 (s, 2H), 2.49 (s, 3H), 1.89 (s, 3H), 1.42 (s, 6H).

Production Example 10-1

2-Chloro-N-(3-methoxy-5-methylpyrazin-2-yl)pyridine-3-sulfonamide

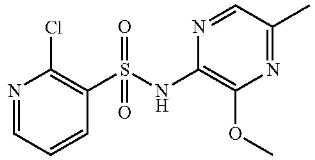 [SMILES: COc1nc(C)cnc1NS(=O)(=O)c1cccnc1Cl]

To a mixture of 3-methoxy-5-methylpyrazin-2-amine (0.2 g, 1.4 mmol) and pyridine (5 mL), 4-dimethylaminopyridine (17.5 mg, 0.143 mmol) and 2-chloropyridine-3-sulfonyl chloride (366 mg, 1.73 mmol) were gradually added at room temperature, and the reaction mixture was stirred at 70° C. for 16 hours. The reaction mixture was brought back to room temperature, and ice-cold water was added thereto, followed by extraction with ethyl acetate. The organic layer was washed with 6 N hydrochloric acid and dried over sodium sulfate, and the solvent was distilled off under reduced pressure. The residue was purified by silica gel column chromatography (hexane/ethyl acetate) to obtain the title compound (0.16 g).

ESI-MS: m/z 315.0 [M+1]+

Production Example 10-2

2-Chloro-N-(3-methoxy-5-methylpyrazin-2-yl)-N-((2-(trimethylsilyl)ethoxy)methyl)pyridine-3-sulfonamide

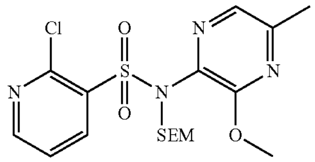 [SMILES: COc1nc(C)cnc1N(COCC[Si](C)(C)C)S(=O)(=O)c1cccnc1Cl]

To a mixture of 2-chloro-N-(3-methoxy-5-methylpyrazin-2-yl)pyridine-3-sulfonamide (50 mg, 0.16 mmol) and N, N-dimethylformamide (2 mL), potassium carbonate (44 mg, 0.32 mmol) was gradually added at 0° C., and the mixture was stirred at the same temperature as above for 30 minutes. 2-(Trimethylsilyl)ethoxymethyl chloride (0.1 mL, 0.24 mmol) was gradually added to the reaction mixture, and the mixture was stirred at room temperature for 30 minutes. Ice-cold water was added to the reaction mixture, followed by extraction with ethyl acetate. The organic layer was washed with saturated saline and dried over sodium sulfate, and the solvent was distilled off under reduced pressure. The residue was purified by silica gel column chromatography (hexane/ethyl acetate) to obtain the title compound (40 mg).

ESI-MS: m/z 445.0 [M+1]+

Production Example 10-3

N-(3-Methoxy-5-methylpyrazin-2-yl)-2-((triisopropylsilyl) ethynyl)-N-((2-(trimethylsilyl)ethoxy) methyl)pyridine-3-sulfonamide

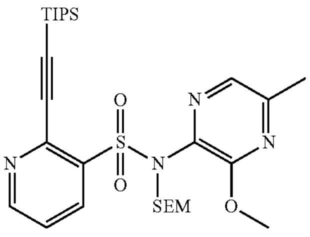

In an argon atmosphere, to a mixture of 2-chloro-N-(3-methoxy-5-methylpyrazin-2-yl)-N-((2-(trimethylsilyl) ethoxy)methyl)pyridine-3-sulfonamide (0.4 g, 0.9 mmol), triethylamine (0.4 mL, 2.7 mmol), triisopropylsilylacetylene (0.3 mL, 1.3 mmol), and N, N-dimethylformamide (5 mL), bis(triphenylphosphine)palladium(II) dichloride (63 mg, 0.089 mmol) and copper(I) iodide (34.2 mg, 0.179 mmol) were added, and the reaction mixture was stirred at 100° C. for 5 hours. The reaction mixture was brought back to room temperature, and filtered through celite while washed with ethyl acetate. The filtrate was washed with water and saturated saline and dried over sodium sulfate, and the solvent was distilled off under reduced pressure. The residue was purified by silica gel column chromatography (hexane/ethyl acetate) to obtain the title compound (160 mg).

ESI-MS: m/z 591.55 [M+1]+

Production Example 10-4

2-Ethynyl-N-(3-methoxy-5-methylpyrazin-2-yl)-N-((2-(trimethylsilyl)ethoxy)methyl)pyridine-3-sulfonamide

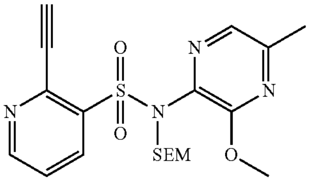 [SMILES: C#Cc1ncccc1S(=O)(=O)N(COCC[Si](C)(C)C)c1ncc(C)nc1OC]

To a mixture of N-(3-methoxy-5-methylpyrazin-2-yl)-2-((triisopropylsilyl) ethynyl)-N-((2-(trimethylsilyl)ethoxy) methyl)pyridine-3-sulfonamide (0.16 g, 0.27 mmol) and tetrahydrofuran (5 mL), tetrabutylammonium fluoride (1 mol/L solution in tetrahydrofuran, 0.27 mL, 0.27 mmol) was gradually added at 0° C., and the reaction mixture was stirred at room temperature for 2 hours. Water was added to the reaction mixture, followed by extraction with ethyl acetate. The organic layer was dried over sodium sulfate, and the solvent was distilled off under reduced pressure. The residue was purified by silica gel column chromatography (hexane/ethyl acetate) to obtain the title compound (80 mg).

ESI-MS: m/z 435.2 [M+1]+

Production Example 10-5

N-(3-Methoxy-5-methylpyrazin-2-yl)-2-((3,3,6-trimethyl-1,3-dihydroisobenzofuran-5-yl)ethynyl)-N-((2-(trimethylsilyl)ethoxy)methyl)pyridine-3-sulfonamide

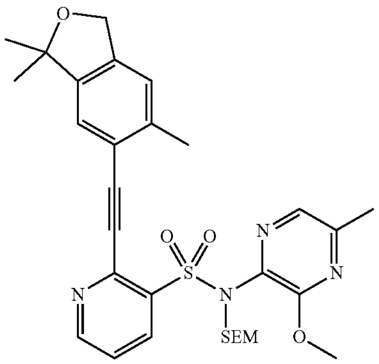

In an argon atmosphere, to a mixture of 2-ethynyl-N-(3-methoxy-5-methylpyrazin-2-yl)-N-((2-(trimethylsilyl) ethoxy)methyl)pyridine-3-sulfonamide (200 mg, 0.460 mmol) and N, N-dimethylformamide (5 mL), 6-iodo-1,1,5-trimethyl-1,3-dihydroisobenzofuran (146 mg, 0.506 mmol), copper(I) iodide (9 mg, 0.046 mmol), triethylamine (0.2 mL, 1.38 mmol), and tetrakis(triphenylphosphine)palladium(0) (53 mg, 0.046 mmol) were added, and the reaction mixture was stirred at room temperature for 1 hour. Ice-cold water was added to the reaction mixture, followed by extraction with ethyl acetate. The organic layer was washed with saturated saline and dried over sodium sulfate, and the solvent was distilled off under reduced pressure. The residue was purified by silica gel column chromatography (hexane/ethyl acetate) to obtain the title compound (170 mg).

ESI-MS: m/z 595.4 [M+1]+

Example 10

N-(3-Methoxy-5-methylpyrazin-2-yl)-2-((3,3,6-trimethyl-1,3-dihydroisobenzofuran-5-yl)ethynyl)pyridine-3-sulfonamide

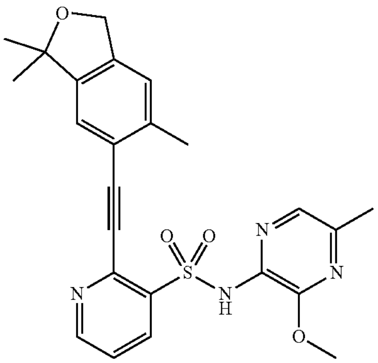

To a mixture of N-(3-methoxy-5-methylpyrazin-2-yl)-2-((3,3,6-trimethyl-1,3-dihydroisobenzofuran-5-yl)ethynyl)-N-((2-(trimethylsilyl)ethoxy)methyl)pyridine-3-sulfonamide (200 mg, 0.336 mmol) and methanol (5 mL), 50% sulfuric acid (3 mL) was added at 0° C., and the reaction mixture was stirred at 60° C. for 1 hour. The solvent in the reaction mixture was distilled off under reduced pressure, and a saturated aqueous solution of sodium bicarbonate was added to the residue, followed by extraction with ethyl acetate. The organic layer was washed with saturated saline and dried over sodium sulfate, and the solvent was distilled off under reduced pressure. The residue was purified by high-performance liquid chromatography (Luna C18 (250×50 mm) 10 μm, 0.1% aqueous formic acid solution/acetonitrile) to obtain the title compound (35 mg).

ESI-MS: m/z 465.35 [M+1]+

1H NMR (400 MHZ, DMSO-d6): δ 10.98 (s, 1H), 8.79 (d, J=4.0 Hz, 1H), 8.36 (dd, J=1.6, 8.0 Hz, 1H), 7.62 (dd, J=4.8, 8.4 Hz, 1H) 7.51 (s, 1H), 7.22 (s, 1H), 4.95 (s, 2H), 3.80 (s, 3H), 2.44 (s, 3H), 2.22 (s, 3H), 1.44 (s, 6H).

Production Example 11-1

(E)-N'-(2-Hydroxy-4-methylbenzylidene)acetohydrazide

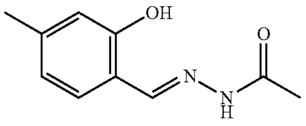

To a mixture of 2-hydroxy-4-methylbenzaldehyde (3.0 g, 22 mmol) and ethanol (40 mL), acetohydrazide (1.64 g, 22.1 mmol) was added at room temperature, and the reaction mixture was stirred at 90° C. for 16 hours. The solvent in the reaction mixture was distilled off under reduced pressure, and the residue was washed with hexane to obtain the title compound (3.0 g) in a crude form. This compound was used in the next reaction without being further purified.

Production Example 11-2

2-Acetyl-4-methylbenzaldehyde

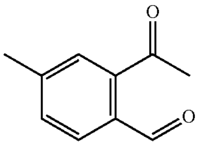

To a mixture of (E)-N'-(2-hydroxy-4-methylbenzylidene) acetohydrazide (4.6 g, 24 mmol) and tetrahydrofuran (50 mL), lead(IV)acetate (11.7 g, 26.3 mmol) was added at 0° C., and the reaction mixture was stirred at room temperature for 16 hours. The reaction mixture was filtered through celite while washed with ethyl acetate. The filtrate was washed with a saturated aqueous solution of sodium bicarbonate and saturated saline and dried over sodium sulfate, and the solvent was distilled off under reduced pressure. The residue was purified by silica gel column chromatography (hexane/ethyl acetate) to obtain the title compound (2.0 g).

1H NMR (400 MHZ, CDCl3): δ10.19 (d, J=4 Hz, 1H), 7.84-7.81 (m, 1H), 7.46 (t, J=6.8 Hz, 2H), 2.65 (d, J=4 Hz, 3H), 2.50 (d, J=3.6 Hz, 3H)

Production Example 11-3

1-(2-(Hydroxymethyl)-5-methylphenyl)ethan-1-ol

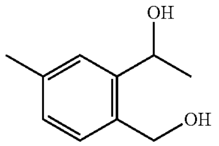

To a mixture of 2-acetyl-4-methylbenzaldehyde (1.4 g, 8.0 mmol), tetrahydrofuran (3.8 mL), and ethanol (11.2 mL), sodium borohydride (1.5 g, 40 mmol) was added at 0° C., and the reaction mixture was stirred at 70° C. for 2 hours. The reaction mixture was brought back to room temperature, and ice-cold water was added to the reaction mixture, followed by extraction with ethyl acetate. The organic layer was washed with a saturated aqueous solution of sodium bicarbonate and saturated saline and dried over sodium sulfate, and the solvent was distilled off under reduced pressure. The residue was purified by silica gel column chromatography (hexane/ethyl acetate) to obtain the title compound (0.85 g).

1H NMR (400 MHZ, CDCl3): δ7.27 (s, 1H), 7.20 (d, J=7.6 Hz, 1H), 6.83 (d, J=7.2 Hz, 1H), 5.01-4.91 (m, 3H), 4.53-4.46 (m, 2H), 2.27 (s, 3H), 1.28 (d, J=6.4 Hz, 3H).

Production Example 11-4

1,6-Dimethyl-1,3-dihydroisobenzofuran

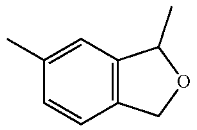

To a mixture of 1-(2-(hydroxymethyl)-5-methylphenyl) ethan-1-ol (0.90 g, 5.4 mmol) and tetrahydrofuran (10 mL), 60% sodium hydride (0.52 g, 13.6 mmol) was gradually added at 0° C., and the mixture was stirred at the same temperature as above for 30 minutes. Trimethyl phosphate (1.5 mL, 13.6 mmol) was added to the reaction mixture at room temperature, and the mixture was stirred at the same temperature as above for 16 hours. Water was added to the reaction mixture, followed by extraction with ethyl acetate. The organic layer was washed with saturated saline and dried over sodium sulfate, and the solvent was distilled off under reduced pressure. The residue was purified by silica gel column chromatography (hexane/ethyl acetate) to obtain the title compound (0.6 g).

1H NMR (400 MHZ, CDCl3): δ7.12-7.07 (m, 2H), 6.98 (d, J=5.2 Hz, 1H), 5.31-5.28 (m, 1H), 5.13-5.00 (m, 2H), 2.39 (d, J=5.2 Hz, 3H), 1.52-1.48 (m, 3H).

Production Example 11-5

5-Bromo-1,6-dimethyl-1,3-dihydroisobenzofuran

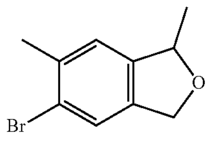

To a mixture of 1,6-dimethyl-1,3-dihydroisobenzofuran (600 mg, 4.05 mmol) and dichloromethane (10 mL), N-bromosuccinimide (721 mg, 4.05 mmol) and trifluoromethanesulfonic acid (1.8 g, 12.2 mmol) were added at 0° C., and the mixture was stirred at room temperature for 2 hours. Ice-cold water was added to the reaction mixture, followed by extraction with ethyl acetate. The organic layer was washed with saturated saline and dried over sodium sulfate, and the solvent was distilled off under reduced pressure. The residue was purified by silica gel column chromatography (hexane/ethyl acetate) to obtain the title compound (0.3 g).

1H NMR (400 MHZ, CDCl3): δ7.51 (d, J=5.2 Hz, 1H), 7.26 (d, J=5.2 Hz, 1H), 5.17-5.12 (m, 1H), 4.96 (d, J=12.8 Hz, 1H), 4.88-4.84 (m, 1H), 2.35 (d, J=5.2 Hz, 3H), 1.37 (t, J=6 Hz, 3H).

Production Example 11-6

2-((1,6-Dimethyl-1,3-dihydroisobenzofuran-5-yl) ethynyl)-N-(4,5-dimethylisoxazol-3-yl)-N-(methoxymethyl)pyridine-3-sulfonamide

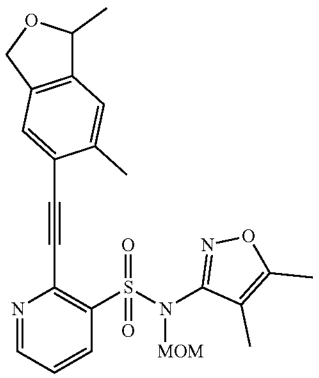

In an argon atmosphere, to a mixture of N-(4,5-dimethylisoxazol-3-yl)-2-ethynyl-N-(methoxymethyl)pyridine-3-sulfonamide (0.40 g, 1.24 mmol) and N, N-dimethylformamide (5 mL), 5-bromo-1,6-dimethyl-1,3-dihydroisobenzofuran (0.337 g, 1.49 mmol), copper(I) iodide (47 mg, 0.249 mmol), triethylamine (0.36 mL, 2.49 mmol), and tetrakis(triphenylphosphine)palladium(0) (143 mg, 0.124 mmol) were added, and the reaction mixture was stirred at 80° C. for 4 hours. The reaction mixture was brought back to room temperature, and water was added thereto, followed by extraction with ethyl acetate. The organic layer was washed with saturated saline and dried over sodium sulfate, and the solvent was distilled off under reduced pressure. The residue was purified by high-performance liquid chromatography (Luna C18 (250×50 mm) 10 μm, 0.1% aqueous formic acid solution/acetonitrile) to obtain the title compound (25 mg).

ESI-MS: m/z 468.23 [M+1]+

Example 11

2-((1,6-Dimethyl-1,3-dihydroisobenzofuran-5-yl) ethynyl)-N-(4,5-dimethylisoxazol-3-yl)pyridine-3-sulfonamide

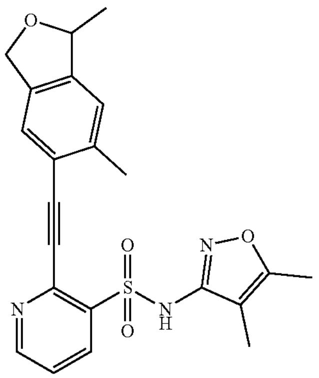 [SMILES: Cc1cc2c(cc1C#Cc1ncccc1S(=O)(=O)Nc1noc(C)c1C)COC2C]

To a mixture of 2-((1,6-dimethyl-1,3-dihydroisobenzofuran-5-yl)ethynyl)-N-(4,5-dimethylisoxazol-3-yl)-N-(methoxymethyl)pyridine-3-sulfonamide (30 mg, 0.064 mmol) and methanol (5 mL), 6 mol/L hydrochloric acid (0.5 mL) was added at 0° C., and the reaction mixture was stirred at 50° C. for 4 hours. The reaction mixture was brought back to room temperature, and ice-cold water was added thereto, followed by extraction with ethyl acetate. The organic layer was washed with a saturated aqueous solution of sodium bicarbonate and saturated saline and dried over sodium sulfate, and the solvent was distilled off under reduced pressure. The residue was purified by high-performance liquid chromatography (Luna C18 (250×50 mm) 10 μm, 0.1% aqueous formic acid solution/acetonitrile) to obtain the title compound (5 mg).

ESI-MS: m/z 424.0 [M+1]+

1H NMR (400 MHZ, DMSO-d6): δ11.02 (s, 1H), 8.81 (d, J=5.2 Hz, 1H), 8.34 (t, J=8 Hz, 1H), 7.63 (t, J=4.4 Hz, 1H), 7.48 (d, J=5.6 Hz, 1H), 7.26 (d, J=5.6 Hz, 1H), 5.22 (d, J=5.6 Hz, 1H), 5.05-5.00 (m, 1H), 4.92 (t, J=6.4 Hz, 1H), 2.48 (d, J=8.8 Hz, 3H), 2.09 (d, J=6.4 Hz, 3H), 1.81 (d, J=6.4 Hz, 3H), 1.41 (t, J=6 Hz, 3H).

Comparative Example 1

In Comparative Example 1, sitaxentan represented by the following formula was used.

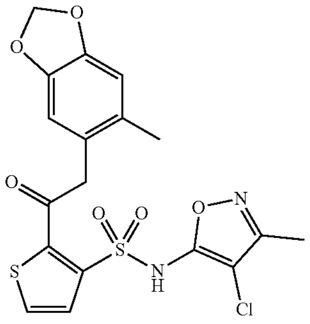 [SMILES: Cc1cc2c(cc1CC(=O)c1sccc1S(=O)(=O)Nc1onc(C)c1Cl)OCO2]

Comparative Example 2

In Comparative Example 2, a compound represented by the following formula was used. This compound is the compound described in Example 1 of International Publication No. WO 2013/115162.

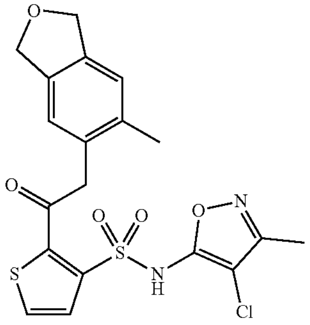 [SMILES: Cc1cc2c(cc1CC(=O)c1sccc1S(=O)(=O)Nc1onc(C)c1Cl)COC2]

Test Example 1-1: Endothelin a Receptor Inhibitory Effect

The inhibitory effect on an endothelin A receptor was studied by the following method.

CHO-K1-mt aequorin cells forced to express a human endothelin A receptor (Accession Number NP_001948.1) were cultured in an antibiotic-free medium for 18 hours, then treated with PBS-EDTA (5 mM EDTA), centrifuged (2 min, 405×g, room temperature), and then suspended in an assay buffer (DMEM/HAM's F12 with HEPES+0.1% BSA protease free).

$1\times10^6$ cells/mL of the cells were incubated at room temperature for 4 hours in the presence of coelenterazine h (Molecular Probes, Inc.) (final concentration: 5 UM). Agonistic reaction based on endothelin was confirmed to determine an endothelin concentration corresponding to EC80.

Subsequently, 50 UL (10000 cells/well) of the cell suspension treated with coelenterazine h and 50 UL of an assay buffer containing a test substance (final concentration: 0.5% in DMSO) were added to each well of a 96-well plate. 15 minutes later, endothelin was added such that its final concentration was an EC80 concentration. Receptor activity was measured as the quantity of light emission in FDSS6000 (Hamamatsu Photonics K.K.). IC50 values were calculated using XLfit (ID Business Solutions Ltd. (IDBS)).

A sample that had an IC50 value of 1.0 nM or lower or exhibited an inhibitory effect of 50% or more at 1.0 nM was given "A"; a sample that had an IC50 value of higher than 10 nM or exhibited an inhibitory effect of less than 50% at 10 nM was given "C"; A sample between "A" and "C" was given "B". The results are shown in Table 1-1.

TABLE 1-1

| ETA receptor inhibitory effect | |
|---|---|
| Example 1 | A |
| Example 2 | A |
| Example 3 | A |
| Example 4 | A |
| Example 5 | B |
| Example 6 | B |
| Example 7 | A |
| Example 8 | A |
| Example 9 | A |
| Example 10 | A |
| Example 11 | B |
| Comparative Example 1 | B |
| Comparative Example 2 | A |

Test Example 1-2: Endothelin B Receptor Inhibitory Effect

The inhibitory effect on an endothelin B receptor was studied by the following method.

CHO-K1-mt aequorin cells forced to express a human endothelin B receptor (Accession Number NP_000106.1) were cultured in an antibiotic-free medium for 18 hours, then treated with PBS-EDTA (5 mM EDTA), centrifuged (2 min, 405×g, room temperature), and then suspended in an assay buffer (DMEM/HAM's F12 with HEPES+0.1% BSA protease free).

$1\times10^6$ cells/mL of the cells were incubated at room temperature for 4 hours in the presence of coelenterazine h (Molecular Probes, Inc.) (final concentration: 5 UM). Agonistic reaction based on endothelin was confirmed to determine an endothelin concentration corresponding to EC80.

Subsequently, 50 UL (10000 cells/well) of the cell suspension treated with coelenterazine h and 50 UL of an assay buffer containing a test substance (final concentration: 0.5% in DMSO) were added to each well of a 96-well plate. 15 minutes later, endothelin was added such that its final concentration was an EC80 concentration. Receptor activity was measured as the quantity of light emission in FDSS6000 (Hamamatsu Photonics K.K.).

A sample that had an IC50 value of 1000 nM or lower or exhibited an inhibitory effect of 50% or more at 1000 nM was given "A"; a sample that had an IC50 value of higher than 5000 nM or exhibited an inhibitory effect of less than 50% at 5000 nM was given "C"; A sample between "A" and "C" was given "B". The results are shown in Table 1-2.

TABLE 1-2

| ETB receptor inhibitory effect | |
|---|---|
| Example 1 | C |
| Example 2 | C |
| Example 3 | C |
| Example 4 | C |
| Example 5 | C |
| Example 6 | C |
| Example 7 | 57% inhibition at 5000 nM |
| Example 8 | C |
| Example 9 | C |
| Example 10 | C |

TABLE 1-2-continued

| ETB receptor inhibitory effect | |
|---|---|
| Example 11 | C |
| Comparative Example 1 | C |
| Comparative Example 2 | C |

As for ETA selectivity, a sample that satisfied any one of the following conditions was given "++".

1. ETB IC50 value/ETA IC50 value of higher than 5000
2. Exhibiting an ETA inhibitory effect of 50% or more at 1.0 nM and an ETB inhibitory effect of less than 50% at 5000 nM A sample that had ETB IC50 value/ETA IC50 value of higher than 1000 and 5000 or lower was given "+".

The results are shown in Table 1-3.

TABLE 1-3

| ETA selectivity (ETB/ETA) | |
|---|---|
| Example 1 | ++ |
| Example 2 | ++ |
| Example 3 | ++ |
| Example 4 | ++ |
| Example 8 | ++ |
| Example 9 | ++ |
| Example 10 | ++ |
| Comparative Example 1 | ++ |
| Comparative Example 2 | ++ |

Test Example 2: CYP2C9 Inhibitory Effect

The inhibitory effect on CYP2C9 was evaluated by the following method.

(1) A frozen liver microsome fraction was thawed on ice and diluted with a potassium phosphate buffer (PPB) to a final concentration of 0.5 mg/mL.

(2) A substrate for evaluation (diclofenac: D6899 from Sigma-Aldrich Co. LLC) was added thereto such that its final concentration was 2.5 μM.

(3) The mixture was slowly mixed and incubated at 37±1° C. for 5 minutes to prepare a reaction solution.

(4) 801 μL of the reaction solution was dispensed to each tube, and an evaluation compound serially diluted with 0.9 μL of DMSO was added thereto such that its final concentration was 9.1 to 20000 nM (⅓ dilutions with 8 concentrations). In this context, 0.9 μL of DMSO was added to a negative control group, and 0.9 μL of sulfaphenazole (S0758 from Sigma-Aldrich Co. LLC) adjusted to a final concentration of 1 μM with DMSO was added to a positive control group.

(5) After mixing, a 270 μL aliquot was transferred to each of two fresh tubes and incubated in a shaking water bath at 37±1° C. for 5 minutes.

(6) Reaction was started by the addition of 30 μL of 10 mM NADPH, and the tubes were incubated at 37° C.±1° C. for 10 minutes.

(7) The tubes were taken out of the shaking water bath, and the reaction was terminated by the addition of 300 μL of a reaction stop solution. After mixing, the tubes were centrifuged at 1021×g at 4° C. for 20 minutes.

(8) The amount of the substrate for evaluation metabolized was determined by LC-MS/MS to calculate the rate of inhibition at each concentration of the evaluation compound.

(9) IC50 values were calculated using GraphPad Prism5. A sample having an IC50 value of 1 μM or lower was given "++"; a sample having an IC50 value in the range of higher than 1 μM and 10 μM or lower was given "+"; and a sample having an IC50 value of higher than 10 μM was given "–". The results are shown in Table 2.

TABLE 2

| | CYP2C9 inhibitory effect |
|---|---|
| Example 1 | – |
| Example 3 | – |
| Example 4 | – |
| Example 5 | – |
| Example 6 | + |
| Example 7 | + |
| Example 8 | – |
| Example 9 | + |
| Example 10 | – |
| Comparative Example 1 | ++ |
| Comparative Example 2 | ++ |

Test Example 3: Metabolic Stability in Human and Mouse Liver Microsomes

The metabolic stability in a human liver microsome was evaluated by the following method.

1. Material (1) Human liver microsome: 20 mg/mL (2) Test compound: 1.1 mM solution in DMSO (3) Potassium phosphate buffer solution: 66.7 mM (pH 7.4)

(4) NADPH solution: 10 mM in a potassium phosphate buffer solution (5) Quenching solution: 0.5% formic acid solution in acetonitrile containing warfarin as an internal standard 2. Method 971.5 μL of the potassium phosphate buffer solution and 27.5 μL of the human liver microsome were placed in a propylene tube and suspended. 1 μL of the test compound was added thereto, and a 180 μL aliquot of this mixture was transferred to a fresh tube. The mixture was preincubated at 37° C. for 5 minutes. Then, 20 μL of the NADPH solution (for an incubation time of 30 minutes) or 20 μL of the potassium phosphate buffer solution (for an incubation time of 0 minutes) was added thereto. After incubation, the reaction was terminated by the addition of 200 μL of the quenching solution. Subsequently, the tube was centrifuged at 3220×g for 20 minutes, and the concentration of an unchanged form of the test compound in 200 ML of a supernatant was measured by LC-MS/MS. On the basis of the obtained peak area of the unchanged form, the residual rate (%) of the unchanged form was calculated using the rate of 0 minutes of incubation time as 100%.

The metabolic stability in a mouse liver microsome was evaluated by the same method as above except that the mouse liver microsome was used instead of the human liver microsome. The residual rate (%) of the unchanged form after 30 minutes are shown in Table 3.

TABLE 3

| | Metabolic stability (human) | Metabolic stability (mouse) |
|---|---|---|
| Example 1 | 59 | 85 |
| Example 3 | 47 | 85 |
| Example 4 | 49 | 91 |
| Example 5 | 63 | 90 |
| Example 6 | 56 | 54 |
| Example 7 | 44 | 81 |
| Example 8 | 73 | 40 |
| Example 9 | 28 | 5 |
| Example 10 | 66 | 68 |

Test Example 4: PAMPA Membrane Permeability Test

The membrane permeability test was carried out using PAMPA. The specific method is as follows.

(1) Lecithin was added at 2% (w/v) into a dodecane solution and completely dissolved.

(2) 5 μL of the lecithin/dodecane solution was added to each well of a donor plate. In this respect, a pipette tip was positioned in no contact with the membrane.

(3) Immediately thereafter, 150 μL of a donor solution (5% DMSO-PBS) containing an evaluation compound (10 μM) was added to each well of the donor plate, and 300 μL of an aqueous buffer was added to each well of a PTFE acceptor plate.

(4) The donor plate filled with the donor solution containing the evaluation compound was slowly placed on the acceptor plate, and the undersurface of the membrane was confirmed to be in contact with the buffer in all the wells.

(5) After covering, the apparatus was incubated at room temperature for 16 hours.

(6) After incubation, 100 μL of the solution was recovered from each of the upper surface and the undersurface of the membrane in the acceptor plate, and acetonitrile containing an equal amount of an internal standard was added thereto.

(7) The concentration of the evaluation compound was measured to calculate a permeation rate.

The results are shown in Table 4. A sample having a membrane permeation rate value of $1\times10^{-8}$ cm/sec or lower was given "C"; a sample having a value in the range of higher than $1\times10^{-8}$ cm/sec and $10\times10^{-8}$ cm/sec or lower was given "B"; and a sample having a value of higher than $10\times10^{-8}$ cm/sec was given "A".

TABLE 4

| | Membrane permeation rate |
|---|---|
| Example 1 | A |
| Example 3 | A |
| Example 4 | C |
| Example 5 | B |
| Example 6 | A |
| Example 7 | A |
| Example 8 | B |
| Example 9 | A |
| Example 10 | A |

Test Example 5: BigET-1-Induced Blood Pressure Evaluation Test

Each 8- to 20-week-old male Wistar rat was subjected to tracheal catheter treatment for airway management, carotid catheter treatment for blood pressure measurement, femoral venous catheter treatment for BigET-1 administration, and duodenal catheter treatment for test substance administration under analgetic treatment and urethane anesthesia. After confirmation that the blood pressure and the heart rate became stable, a vehicle (0.5% methylcellulose 400 solution) or 30 mg/kg (5 ml/kg) of a test substance adjusted with a vehicle was administered into the duodenum. One hour thereafter, BigET-1 (20 μg/kg) was administered thereto, and the blood pressure was monitored until 60 minutes after BigET-1 administration. The test was conducted at n=6 per group. In analysis, systolic blood pressure and diastolic blood pressure were determined for 20 seconds every 5 minutes from 5 minutes before BigET-1 administration to 60 minutes after BigET-1 administration, and AUC0-60 min (mmHg*min) for 60 minutes after BigET-1 administration was calculated using a delta value from the value obtained 5 minutes before BigET-1 administration. The Student's t test was used for the comparison of AUC between the vehicle administration group and the test substance administration group.

TABLE 5

| | Systolic blood pressure delta $AUC_{0\text{-}60\ min}$ | Diastolic blood pressure delta $AUC_{0\text{-}60\ min}$ |
|---|---|---|
| Vehicle group | 3057 ± 1273 | 3191 ± 955 |
| Example 1 | 83 ± 508 # | 278 ± 539 # |
| Example 3 | 113 ± 565 # | 322 ± 435 # |

Mean ± SD, N = 6,
$p < 0.01$ vs vehicle group

What is claimed is:

1. A compound represented by the following formula (1):

(1)

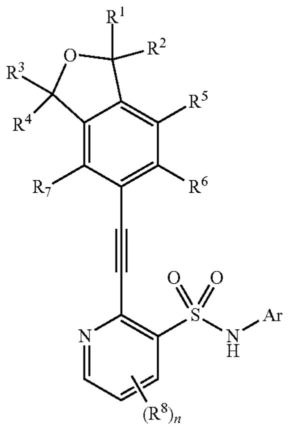

wherein $R^1$ and $R^2$ are each independently hydrogen or alkyl, $R^3$ and $R^4$ are each independently hydrogen or alkyl, or $R^3$ and $R^4$ together form oxo, $R^5$ to $R^7$ are each independently hydrogen, alkyl, haloalkyl, halogen, alkoxy or haloalkoxy, each $R^8$ is independently alkyl, haloalkyl or halogen, n is an integer of 0 to 3, and Ar is represented by the following formula (Ar1) or (Ar2):

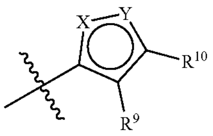

(Ar1)

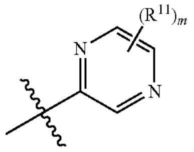

(Ar2)

wherein

X and Y are nitrogen and oxygen, respectively, or oxygen and nitrogen, respectively, $R^9$ and $R^{10}$ are each independently hydrogen, alkyl, haloalkyl or halogen, each $R^{11}$ is independently alkyl, haloalkyl, halogen, alkoxy or haloalkoxy, and m is an integer of 0 to 3, or a pharmaceutically acceptable salt thereof.

2. The compound or the pharmaceutically acceptable salt thereof according to claim 1, wherein each of $R^1$ and $R^2$ is hydrogen.

3. The compound or the pharmaceutically acceptable salt thereof according to claim 1, wherein each of $R^5$ and $R^7$ is hydrogen, and $R^6$ is alkyl.

4. The compound or the pharmaceutically acceptable salt thereof according to claim 1, wherein n is 0.

5. The compound or the pharmaceutically acceptable salt thereof according to claim 1, wherein Ar is represented by formula (Ar1).

6. The compound or the pharmaceutically acceptable salt thereof according to claim 1, wherein each of $R^9$ and $R^{10}$ is alkyl.

7. The compound or the pharmaceutically acceptable salt thereof according to claim 1, wherein X and Y are nitrogen and oxygen, respectively.

8. The compound or the pharmaceutically acceptable salt thereof according to claim 1, wherein X and Y are oxygen and nitrogen, respectively.

9. The compound or the pharmaceutically acceptable salt thereof according to claim 1, wherein Ar is represented by formula (Ar2).

10. The compound or the pharmaceutically acceptable salt thereof according to claim 1, wherein each $R^{11}$ is independently alkyl or alkoxy.

11. The compound or the pharmaceutically acceptable salt thereof according to claim 1, wherein m is 2.

12. The compound or the pharmaceutically acceptable salt thereof according to claim 1, wherein the compound is selected from the group consisting of the following compounds:

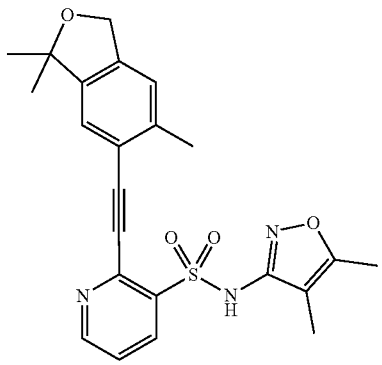

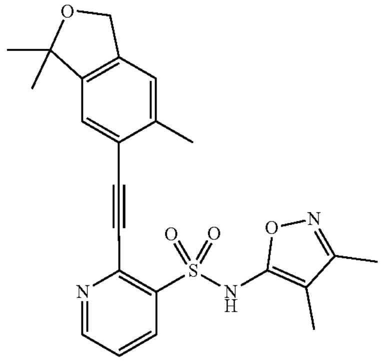

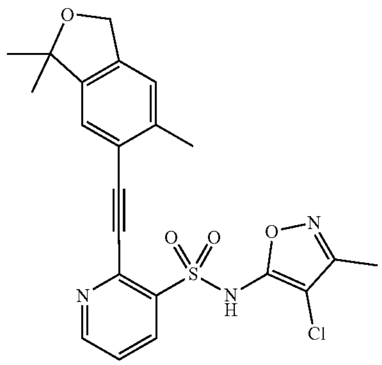

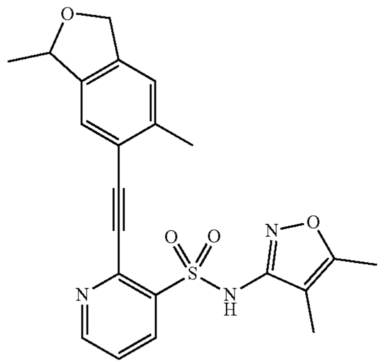

-continued
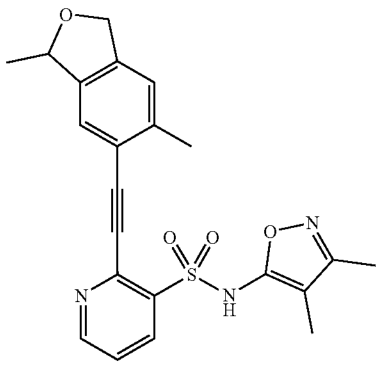
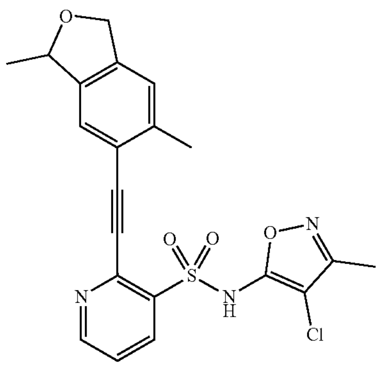
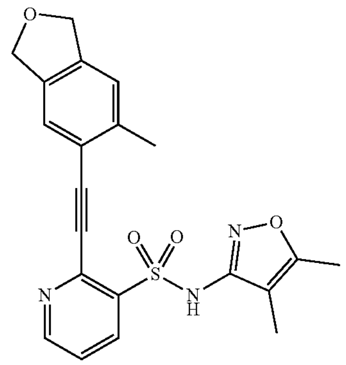
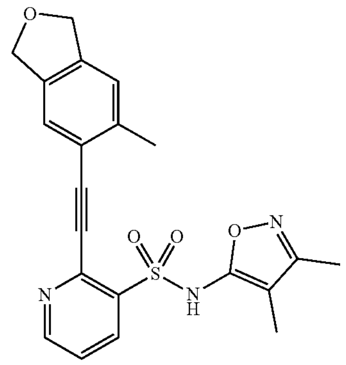
-continued
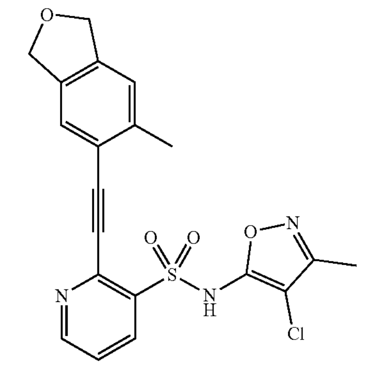
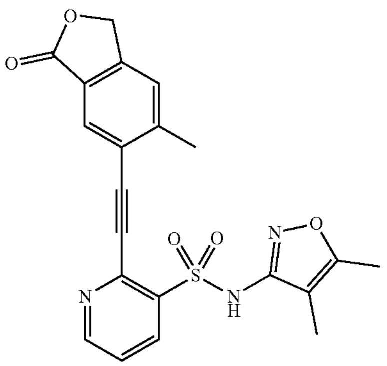
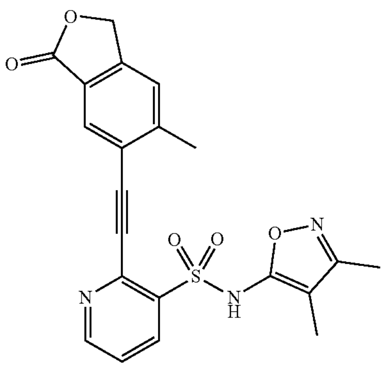
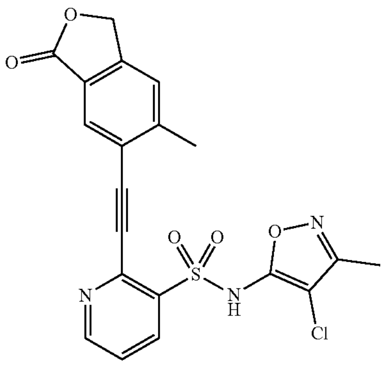

-continued
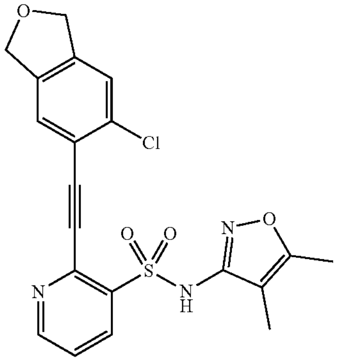
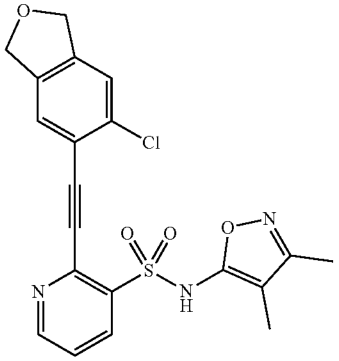
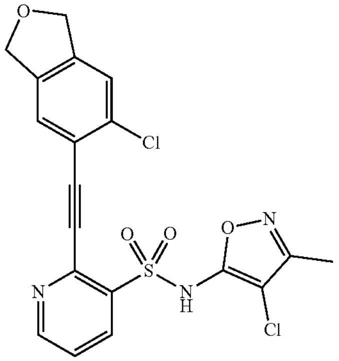
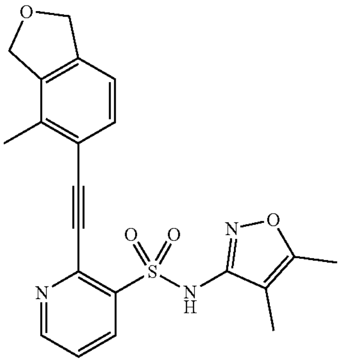
-continued
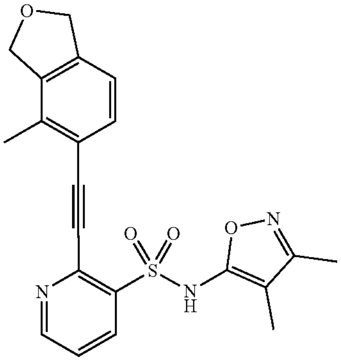
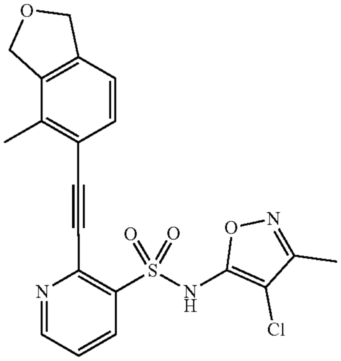
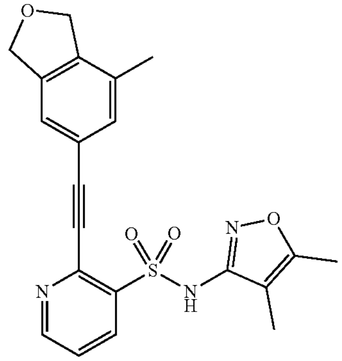
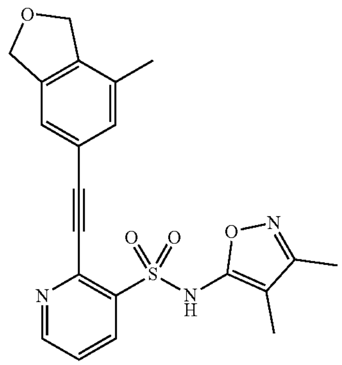

-continued

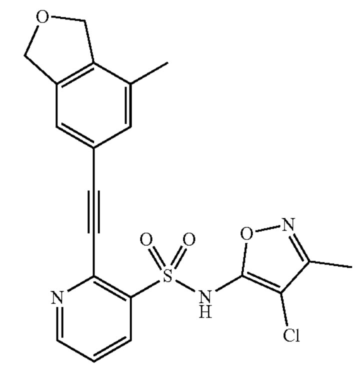

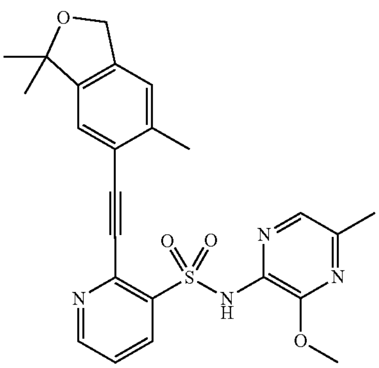

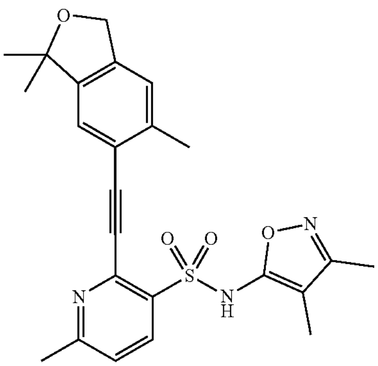

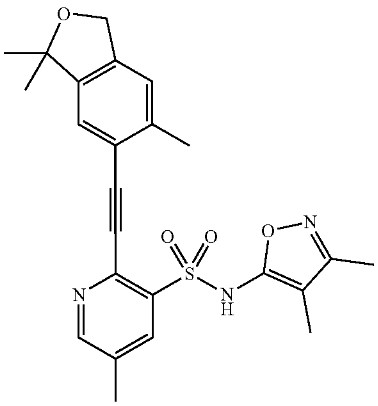

-continued

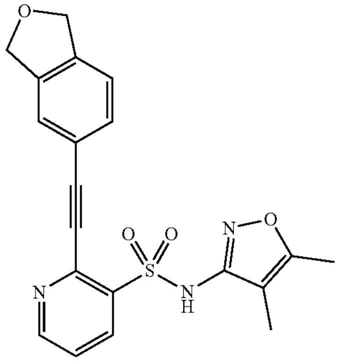

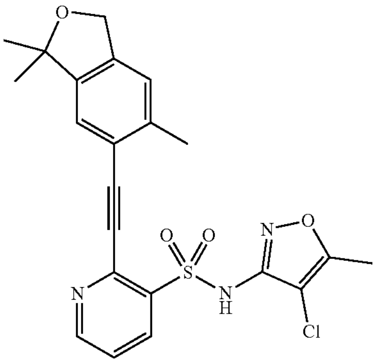

and

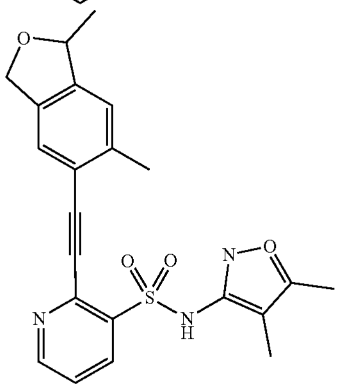

.

13. A method for inhibiting an endothelin A receptor, comprising administering an effective amount of the compound or the pharmaceutically acceptable salt thereof according to claim 1 to a patient in need thereof.

14. The method according to claim 13, wherein the method selectively inhibits the endothelin A receptor in contrast to an endothelin B receptor.

15. A pharmaceutical composition comprising the compound or the pharmaceutically acceptable salt thereof according to claim 1.

16. A method for preventing or treating pulmonary hypertension, nephropathy, hypertension, hepatitis, cancer, pain, heart failure, or vasospasm, comprising administering an effective amount of the compound or the pharmaceutically acceptable salt thereof according to claim 1 to a patient in need thereof.

17. The compound or the pharmaceutically acceptable salt thereof according to claim 1, wherein the compound is

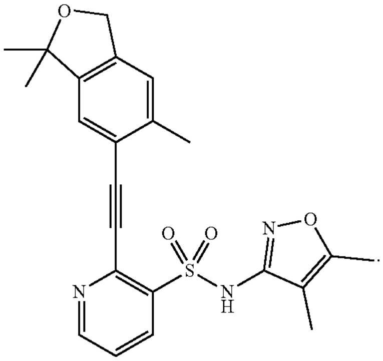
18. The compound or the pharmaceutically acceptable salt thereof according to claim 1, wherein the compound is
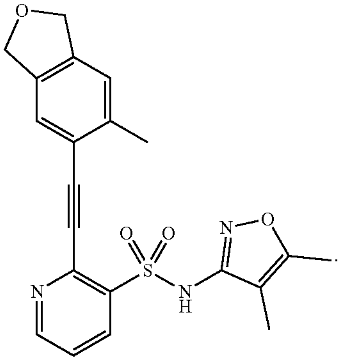 [SMILES: Cc1cc2c(cc1C#Cc1ncccc1S(=O)(=O)Nc1noc(C)c1C)COC2]
19. The compound or the pharmaceutically acceptable salt thereof according to claim 1, wherein the compound is
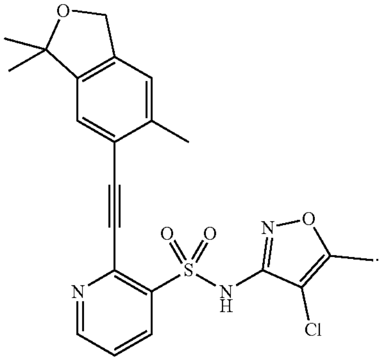
20. The compound or the pharmaceutically acceptable salt thereof according to claim 1, wherein the compound is
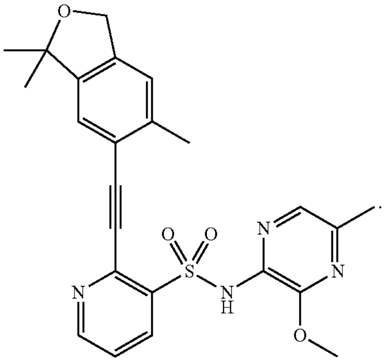
* * * * *